(12) United States Patent
Gurin

(10) Patent No.: US 12,044,644 B2
(45) Date of Patent: Jul. 23, 2024

(54) MULTI-TEMPERATURE GAS SENSING

(71) Applicant: INVENSENSE, INC., San Jose, CA (US)

(72) Inventor: Ilya Gurin, San Jose, CA (US)

(73) Assignee: InvenSense, Inc., San Jose, CA (US)

( * ) Notice: Subject to any disclaimer, the term of this patent is extended or adjusted under 35 U.S.C. 154(b) by 197 days.

(21) Appl. No.: 17/559,839

(22) Filed: Dec. 22, 2021

(65) Prior Publication Data

US 2023/0194454 A1 Jun. 22, 2023

(51) Int. Cl.
| | |
|---|---|
| G01N 27/18 | (2006.01) |
| G01K 7/22 | (2006.01) |
| G01N 33/00 | (2006.01) |
| H05B 3/20 | (2006.01) |

(52) U.S. Cl.
CPC .............. *G01N 27/18* (2013.01); *G01K 7/22* (2013.01); *G01N 33/004* (2013.01); *H05B 3/20* (2013.01)

(58) Field of Classification Search
CPC ...... G01N 27/14; G01N 27/18; G01N 33/004; G01N 27/122; G01N 27/123; G01K 7/22
See application file for complete search history.

(56) References Cited

U.S. PATENT DOCUMENTS

| | | | |
|---|---|---|---|
| 2018/0052129 A1* | 2/2018 | Biancolillo | .......... G01N 27/121 |
| 2019/0353607 A1 | 11/2019 | Kaita | |
| 2021/0003525 A1 | 1/2021 | Kaita et al. | |

FOREIGN PATENT DOCUMENTS

| | | |
|---|---|---|
| CN | 113960119 A | 1/2022 |
| CN | 113960325 A | 1/2022 |
| DE | 102011001028 | 2/2012 |
| DE | 102011107442 A1 | 1/2013 |
| WO | WO2022002824 A2 | 1/2022 |

\* cited by examiner

*Primary Examiner* — Benjamin R Schmitt
(74) *Attorney, Agent, or Firm* — Van Hoven PC; Joshua Van Hoven

(57) ABSTRACT

A gas sensor includes a plurality of sensing resistors that vary in resistance based on ambient temperature and the presence of certain gases, such as $CO_2$ and $H_2O$. The responses of each of the sensing resistors vary based on a base temperature of each of the sensing resistors. The base temperatures for each of the sensing resistors and configurations of the sensing resistors are selected to emphasize a response to a gas of interest (e.g., $CO_2$) while de-emphasizing or canceling contributions from ambient temperature and gases that are not of interest (e.g., $H_2O$).

18 Claims, 9 Drawing Sheets

MULTI-TEMPERATURE GAS SENSING

BACKGROUND

Miniaturized electronic gas sensors may utilize components that change their electrical, chemical and/or mechanical behavior in response to the presence of particular gases. The response of the gas-sensitive components may vary based on a number of factors, such as the temperature of the gas-sensitive components and the presence of gases or environmental conditions that also modify the response of the gas-sensitive components. In many end-use applications, gas sensors are subject to a variety of environments and operating conditions, some of which may compromise the accuracy of the gas sensor due to other impacts on sensor output overwhelming the contribution of the particular gas to the sensor output.

SUMMARY

In an embodiment of the present disclosure, a sensor device including a plurality of sensors comprises a first sensor comprising a first sensing resistor and a first heating element, wherein the first heating element is configured to raise the temperature of the first sensing resistor to a first temperature greater than an ambient temperature, wherein a resistance of the first sensing resistor varies based on a concentration of one or more gases in the ambient air. The first sensor may further comprise a hotplate configured to expose the first sensing resistor and the first heating element to a sample of ambient air and facilitate the raising of the temperature of the first sensing resistor to the first temperature. The sensor device may further comprise a second sensor comprising a second sensing resistor, wherein the second sensor is at an ambient temperature of a sample of ambient air, wherein the first sensing resistor and the second sensing resistor are connected in a first series electrical circuit, and wherein a first measurement node is located between the first sensing resistor and the second sensing resistor in the first series electrical circuit. A resistance of the second sensing resistor may not vary based on the concentration of the one or more gases. The resistances of both the first and second sensing resistors may vary based on the ambient temperature. The sensor device may further comprise processing circuitry coupled to the measurement node, wherein the processing circuitry is configured to determine a concentration of a gas of interest of one of the one or more gases based on a voltage of the first measurement node.

In an embodiment of the present disclosure, a sensor device including a plurality of sensors comprises a first sensor comprising a first sensing resistor and a first heating element, wherein the first heating element is configured to raise the temperature of the first sensing resistor to a first temperature. The sensor device may further comprise a second sensor comprising a second sensing resistor, wherein the second sensing resistor is connected in series to the first sensing resistor, and wherein a measurement node is located between the first sensing resistor and the second sensing resistor. The sensor device may further comprise at least one hotplate configured to expose the first sensing resistor and the second sensing resistor to the ambient air, wherein a resistance of each of the first sensing resistor and the second sensing resistor varies based on a concentration of one or more gases in the ambient air and a respective temperature of each of the sensing resistors. The sensor device may further comprise processing circuitry coupled to the first measurement node and the second measurement node, wherein the processing circuitry is configured to determine a concentration of a gas of interest of one of the one or more gases based on a voltage of the first measurement node and a voltage of the second measurement node. In the context of the present disclosure, a "sensing" resistor will be understood to be a resistor that changes its resistance in response to external stimuli.

In an embodiment of the present disclosure, a sensor device including a plurality of sensors comprises a first sensor comprising a first sensing resistor and a first heating element, wherein the first heating element is configured to raise the temperature of the first sensing resistor to a first temperature. The sensor device further comprises a first reference resistor and a second reference resistor, connected in series to the first sensing resistor, wherein a first measurement node is connected between the first sensing resistor and the first reference resistor and a second measurement node is connected between the first reference resistor and the second reference resistor. The sensor device may further comprise a second sensor comprising a second sensing resistor and a second heating element, wherein the second sensing resistor is connected in series with the second reference resistor, and a third measurement node is connected between the second reference resistor and the second sensing resistor. In the context of the present disclosure, a "reference" resistor will be understood to be a resistor that maintains a constant resistance regardless of external stimuli.

In an embodiment of the present disclosure, a method for operating a sensor device including a plurality of sensors comprises applying, to a first sensor comprising a first sensing resistor, a first temperature, wherein the first temperature is greater than an ambient temperature, and receiving, by the first sensor, a sample of ambient air. The method may further comprise receiving, at a second sensor comprising a second sensing resistor, the sample of ambient air, wherein the second temperature sensor is at an ambient temperature of the sample of ambient air, wherein the first sensing resistor and the second sensing resistor are connected in a first series electrical circuit, and wherein a first measurement node is located between the first sensing resistor and the second sensing resistor in the first series electrical circuit. The method may further comprise receiving, from the first measurement node, a first signal that is based on resistance of the first sensing resistor and second sensing resistor, wherein a resistance of the first sensing resistor varies based on a concentration of one or more gases in the ambient air, a resistance of the second sensing resistor does not vary based on the concentration of the one or more gases while the second sensing resistor is at the ambient temperature, and the resistance of both the first sensing resistor and second sensing resistor vary based on the ambient temperature. The method may further comprise determining, by processing circuitry, the concentration of a gas of interest of one of the one or more gases based on the received first signal.

In an embodiment of the present disclosure, a sensor device comprising two or more measurement nodes, wherein respective voltages at the two or more measurement nodes vary in response to external stimuli, further comprises processing circuitry configured to produce a voltage at an output node, wherein the processing circuitry may multiply a first voltage at each of the two or more measurement nodes by a corresponding gain, wherein a first gain may be unequal to a second gain. In a further embodiment, the processing circuitry may further comprise a temperature sensor, and the first gain may have a first temperature dependence and the second gain may have a second temperature dependence, wherein the first temperature dependence may be unequal to the second temperature dependence. The processing circuitry may comprise analog circuits (e.g., amplifiers), digital circuits (e.g., analog-to-digital converters, multipliers and adders), and temperature sensors (e.g., bandgap references or resistive temperature detectors).

BRIEF DESCRIPTION OF DRAWINGS

The above and other features of the present disclosure, its nature, and various advantages will be more apparent upon consideration of the following detailed description, taken in conjunction with the accompanying drawings in which.

DETAILED DESCRIPTION OF DRAWINGS

Figure 1:
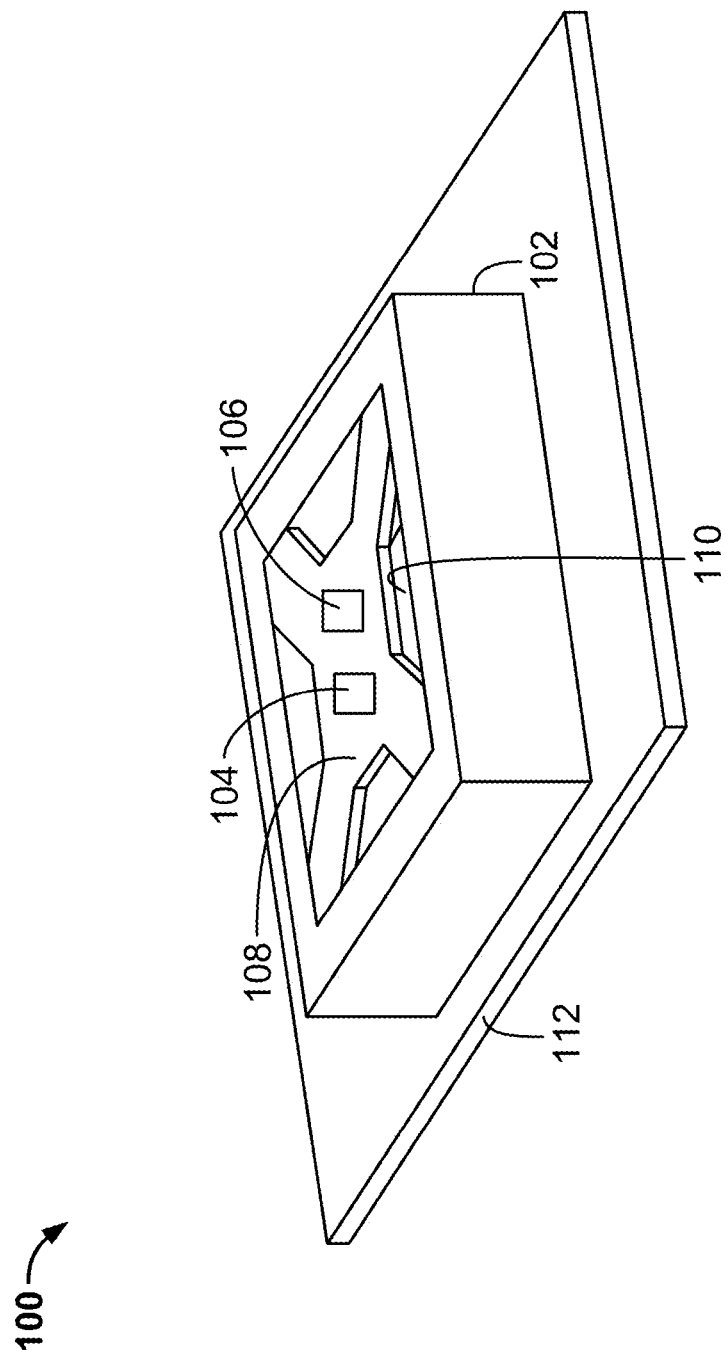
FIG. 1 shows an illustrative gas sensor in accordance with an embodiment of the present disclosure.

A sensor device for sensing a concentration of a gas of interest includes a plurality of individual gas sensors exposed to a common ambient air sample. In the context of the present disclosure, an "ambient" air sample will be understood to be the air in whatever environment the sensor device is exposed to. A component that is at an ambient temperature will be understood to include a range of temperatures about the temperature of the ambient air sample, including plus or minus 10 degrees Celsius. Each of the plurality of gas sensors includes a component such as a sensing resistor that has a base temperature, e.g., 200° C., which may be elevated substantially above ambient temperature, e.g., 25° C., and a resistance that changes over a range of temperatures such as 0° C. to 300° C. The actual temperature of the component may vary about the base temperature, so that if ambient temperature increases to e.g., 35° C., the component temperature may increase to e.g., 305° C. The sensing resistors may also vary their resistance based on concentrations of particular gases that are present in the ambient air sample (e.g., based on the gas concentration changing the temperature of the resistor, which in turn changes the resistance of the resistor). The degree of this variation may in turn be based on the temperatures of the sensing resistors, i.e., such that the response of the sensing resistors to a particular concentration of a gas may be significantly greater at particular temperature ranges, e.g., between 0° C. to 300° C., and on the ambient temperature. For example, the response of the sensing resistors to a particular concentration of a gas may be zero at a particular temperature, e.g., sensing resistor temperature equal to ambient temperature, or significantly greater at another particular temperature, e.g., 200° C. Sensing the changes that result from the responses of the sensing resistors and performing digital processing based on the changes may require a high-precision analog-to-digital conversion, based on the relatively small responses of the sensing resistors. Accordingly, it may be desirable to configure and control the sensing resistors in a manner that facilitates a response that is more easily discernable, for example, by controlling a voltage applied to a heating element.

Each of the plurality of sensing resistors may be heated (or not heated) to particular temperatures to acquire outputs (e.g., voltages that vary based on the changing resistances of the sensing resistors) having particular characteristics. For example, within a temperature range, the response of a sensing resistor to the presence of a first gas may change substantially, e.g., such that at a first temperature at one end of the range there is a proportionally small change in resistance due to the presence of the first gas while at a second temperature at the other end of the temperature range there is a proportionally large change in resistance due to the first gas. Within another temperature range, the proportional change in resistance due to the presence of the first gas may be relatively constant, allowing the selection of hotplate temperatures where different resistors of sensors at different temperatures (and thus, having different responses to other gases or ambient temperature) respond in a similar manner to the first gas, cancelling the effect of the first gas while isolating effects due to other gases and ambient temperature. By selectively setting the temperatures for different sensing resistors to emphasize and/or isolate particular sources of change in resistance, and connecting the sensing resistors to further emphasize, isolate, or cancel these changes, a more accurate determination of the gas of interest may performed.

FIG. 1 depicts an exemplary gas sensor 100 in accordance with some embodiments of the present disclosure. In an embodiment as described herein, the gas sensor 100 may include at least a substrate 112, an enclosure 102, and a hotplate 108. The gas sensor 100 may further include an air sample cavity 110, a first resistor 104, a second resistor 106, and electrical interconnects (not shown).

Substrate 112 and electrical interconnects (not shown) provide physical and electrical coupling of the first resistor 104 and the second resistor 106 to other components of the gas sensor. For example, substrate 112 may include processing circuitry or connections to external processing circuitry that determine a concentration of a gas of interest (e.g., $CO_2$) while removing or otherwise ignoring effects of other gases that are not of interest (e.g., $H_2O$) based on output values of gas sensors (e.g., voltages at intermediate nodes that vary based on changing resistances of the resistors).

Although in some embodiments (not depicted in FIG. 1) the gas sensor or other sensors may communicate directly with external circuitry (e.g., via a serial bus or direct connection to sensor outputs and control inputs), in an embodiment the processing circuitry may process data received from the gas sensor and other sensors and communicate with external components via a communication interface (e.g., a SPI or I2C bus, in automotive applications a controller area network (CAN) or Local Interconnect Network (LIN) bus, or in other applications suitable wired or wireless communications interfaces as is known in the art). The processing circuitry may convert signals received from the gas sensor and other sensors into appropriate measurement units (e.g., based on settings provided by other computing units communicating over the communication bus) and perform more complex processing to determine measurements such as rate of change of gas concentration, and in some embodiments, to determine from sensor data whether a particular change in gas concentration requires issuing messages or warnings, or taking other action such as increasing measurement frequency.

Enclosure 102 provides a boundary condition for heat conduction through air sample cavity 110 and provides physical support for sensor components (e.g., hotplate 108, first resistor 104, and second resistor 106). Enclosure 102 may include electrical connections (e.g., to sensor components) and portions of processing circuitry. Although FIG. 1 depicts enclosure 102 in a particular shape, enclosure 102 can be in any suitable shape to act as a barrier for air sample cavity 110 and provide support for sensor components. In some embodiments, enclosure 102 may include features (e.g., for physical and electrical connection to external components) such that enclosure 102 is a unitary component that also performs the function of substrate 112.

Hotplate 108 is supported by and electrically and physically connected to enclosure 102. Hotplate 108 provides physical support for and electrical connections to the first resistor 104 and the second resistor 106, while also providing an air path to air sample cavity 110. Although FIG. 1 is shown with two sensing elements at particular locations, there can be any suitable number of sensing elements in a variety of locations on the gas sensor. Furthermore, although other figures depict connections to certain circuit components (e.g., heaters, resistors, etc.), hotplate 108 can support additional components and connections. In some embodiments, hotplate 108 includes an opening to air sample cavity 110 below and within enclosure 102. Although FIG. 1 depicts a particular shape of hotplate 108, hotplate 108 can be any suitable shape to provide a suitable air path to sample cavity 110. Hotplate 108 suspends the first resistor 104 and the second resistor 106 above air sample cavity 110 to make gas concentration measurements. Although a particular hotplate 108 configuration is depicted in FIG. 1, it will be understood that a variety of suitable shapes can accommodate multiple sensing elements and electrical connections while providing suitable access to an air sample cavity 110. In some embodiments, hotplate 108 includes thermal film to manage heat generation from the first resistor 104 and the second resistor 106. In some embodiments, hotplate 108 is continuous, and the air sample enters the air sample cavity 110 through a hole in the substrate 112.

Air sample cavity 110 is the space beneath hotplate 108 and surrounded by enclosure 102 that facilitates air flow to the hotplate 108. First resistor 104 is located on hotplate 108 to be exposed to an air sample of interest such as within air sample cavity 110, although gas sensors may also be exposed to air from other suitable locations such as an upper surface of hotplate 108. The thermal conductance of air sample cavity 110 depends on the composition of the air sample, e.g., the concentration of a gas of interest. In some embodiments as described herein, the total thermal conductance between the hotplate 108 and the enclosure 102 is substantially similar (e.g., within 10%) to the thermal conductance of air sample cavity 110. In some other embodiments, the total thermal conductance between the hotplate 108 and the enclosure 102 is substantially similar (e.g., within 10%) of the aggregate thermal conductance of air sample cavity 110 and the air volume adjacent to the upper surface of hotplate 108 (not indicated in the figure). When one or more voltages are applied to one or more heating elements incorporated within hotplate 108, the temperature of hotplate 108 varies according to the thermal conductance of air sample cavity 110.

Although other figures depict the first resistor 104 including certain circuit components, the first resistor 104 can be constructed in a variety of manners. In some embodiments as described herein, the first resistor 104 is configured as a first heating element and coupled to control circuitry (e.g., a voltage source). The first heating element raises the temperature of the hotplate 108, including second resistor 106, to a desired temperature for capturing particular information about an air sample. In some embodiments as described herein, the temperature of hotplate 108 is substantially uniform (e.g., within 10%) when heated by one or more heating elements. For example, the first heating element may raise the temperature of the first sensing resistor to 150° C.

Second resistor 106 is located on hotplate 108 to be exposed to the temperature of hotplate 108. Although other figures depict the second resistor 106 including certain circuit components, the second resistor 106 can be constructed in a variety of manners. In some embodiments as described herein, the second resistor 106 is a temperature-sensitive resistor, such as a thermistor.

Figure 2:
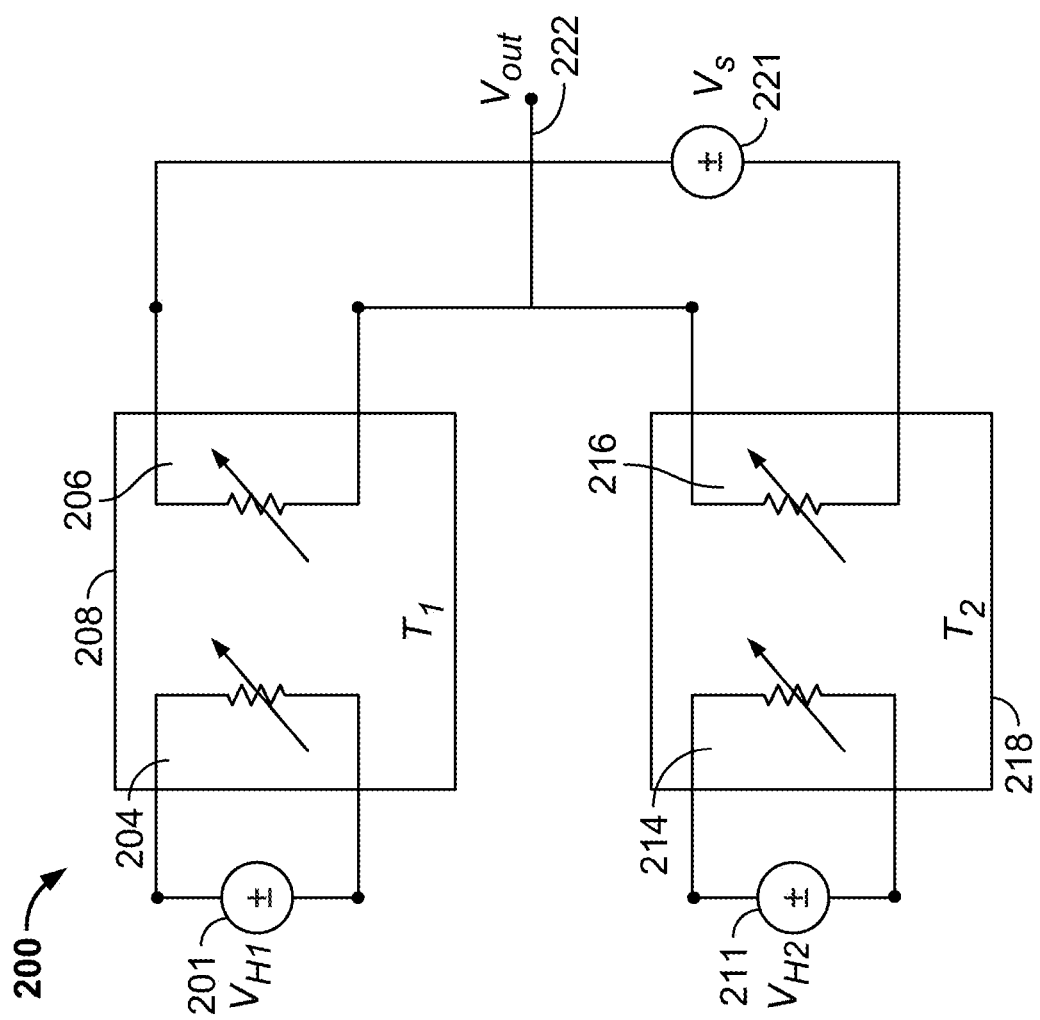
FIG. 2 shows an example circuit diagram of a gas sensor device including a first gas sensor and a second gas sensor in accordance with an embodiment of the present disclosure.

FIG. 2 shows an example circuit diagram of a gas sensor device including a first gas sensor and a second gas sensor in accordance with an embodiment of the present disclosure. Although particular components are depicted for the gas sensor devices described herein, it will be understood that other suitable combinations of sensors, processing components, circuitry components, memory, and other circuitry may be utilized as necessary for different applications and systems. In certain embodiments of the present disclosure, the circuitry, devices, systems, and methods described herein may be described in the context of a gas sensor device for determining a concentration of a gas of interest from an air sample for further processing. However, it will be understood that the circuitry, devices, systems, and methods described herein may be applied to other types of gases of interest.

Control and processing as described herein may be performed by processing circuitry. Portions of any processing circuitry may be split between multiple components of gas sensor devices described herein and/or external devices or components. Processing circuitry may include one or more components providing necessary processing based on the requirements of the gas sensor device. In some embodiments, processing circuitry may include hardware control logic that may be integrated within a chip of a sensor device to control the operation of the gas sensor device or other sensors and perform aspects of processing for the gas sensor device or other sensors. In some embodiments, the gas sensor device and other sensors may include one or more digital registers that allow aspects of the operation of hardware control logic to be modified (e.g., by modifying a value of a register). In some embodiments, processing circuitry may also include a processor such as a microprocessor that executes software instructions (e.g., that are stored in memory). The microprocessor may control the operation of the gas sensor by interacting with the hardware control logic and process signals received from the gas sensor. The microprocessor may interact with other sensors in a similar manner. In some embodiments, some or all of the functions of the processing circuitry, and in some embodiments, of memory, may be implemented on an application specific integrated circuit ("ASIC") and/or a field programmable gate array ("FPGA").

Although the circuit diagram of FIG. 2 includes particular circuit components, it will be understood that components may be substituted, modified, or changed in some embodiments. The exemplary gas sensor device incorporates a first hotplate 208, comprising a first heating element 204 and a first sensing resistor 206, and a second hotplate 218, comprising a second heating element 214 and a second sensing resistor 216. It further incorporates a first heater voltage source $V_{H1}$ 201 and a second heater voltage source $V_{H2}$ 211, with respective nodes connected to the first heating element 204 and the second heating element 214. It further incorporates a third voltage source $V_S$ 221, with respective nodes connected to the first sensing resistor 206 and the second sensing resistor 216, and measurement node 222, connected to the first sensing resistor 206 and the second sensing resistor 216.

First heater voltage source $V_{H1}$ 201 applies the first voltage to the first heating element 204, which causes the first heating element 204 to heat the first hotplate 208 to a first temperature that has particular properties for sensing a gas of interest (e.g., $CO_2$) of the air sample. For example, first heater voltage source $V_{H1}$ 201 may apply the first voltage resulting in the first heating element 204 generating a first base temperature of 150° C.

First sensing resistor 206 receives the first temperature from first heating element 204 and reacts by altering its resistance to a base resistance for sensing the air sample from air sample cavity 110. Subsequently, resistance of first sensing resistor 206 further changes based on properties of the air sample, including temperature and gas content (e.g., $CO_2$ and $H_2O$ content). For example, the first sensing resistor 206 may receive a base temperature of 150° C. from the first heating element 204 and change its resistance accordingly, establishing the base resistance for sensing the air sample, and change its resistance further according to the properties of the air sample (e.g., temperature and gas content). The first sensing resistor 206 in turn is in a series circuit with the second sensing resistor 216. The voltage at output node 222 varies based on the resistance values of the first sensing resistor 206 and the second sensing resistor 216 since the third voltage source $V_S$ 221 is constant. It will be understood in the context of the present disclosure that words such as "when", "then", and "further", referring to temperature or resistance changes, do not necessarily imply a sequence of discrete events, as the changes may occur simultaneously.

Second heater voltage source $V_{H2}$ 211 applies the second voltage to the second heating element 214, which causes the second heating element 214 to heat the second hotplate 218 to a second temperature that has particular properties for sensing a gas of interest (e.g., $CO_2$) of the air sample. For example, second heater voltage source $V_{H2}$ 201 may apply the second voltage resulting in the second heating element 210 generating a second base temperature of 300° C.

Second sensing resistor 216 receives the second temperature from second heating element 214 and reacts by altering its resistance to a base resistance for sensing the air sample from air sample cavity 110. Subsequently, resistance of second sensing resistor 216 further changes based on properties of the air sample, including temperature and gas content (e.g., $CO_2$ and $H_2O$ content). For example, the second sensing resistor 216 may receive a base temperature of 300° C. from the second heating element 214, change its resistance accordingly, establishing the base resistance for sensing the air sample, and change its resistance further according to the properties of the air sample (e.g., temperature and gas content). The resistance in turn is in a series circuit with the first sensing resistor 206. The voltage at output node 222 varies based on the resistance values of the first sensing resistor 206 and the second sensing resistor 216 since the third voltage source $V_S$ 221 is constant.

Voltage source $V_S$ 221 supplies voltage to the series-connected first sensing resistor 206 and second sensing resistor 216. Output node 222 is a voltage divider based on voltage source $V_S$ 221, serving as a constant, and a ratio of the resistance of the first sensing resistor 206 and second sensing resistor 216. The resistance of first sensing resistor 206 initially changes to base resistance for sensing the air sample as a result of the first applied temperature by first heating element 204. Thereafter, resistance of first sensing resistor 206 changes again when in contact with the properties of the air sample (e.g., temperature and gas content of $CO_2$ and $H_2O$) from air sample cavity 110. Resistance of second sensing resistor 216 initially changes to base resistance for sensing the air sample as a result of the second applied temperature by second heating element 214. Thereafter, resistance of second sensing resistor 216 changes again when in contact with the properties of the air sample (e.g., temperature and gas content of $CO_2$ and $H_2O$) from air sample cavity 110. So, the voltage at output node 222 changes according to changes in resistance of the first sensing resistor 206 and the second sensing resistor 216 based on their respective responses to the properties of the air sample. The first applied temperature and the second applied temperature are different, so the response of the first sensing resistor 206 and the second sensing resistor 216 will differ as well. Consequently, an output response of a gas of interest (e.g., $CO_2$) can be determined based on the change in the voltage at output node 222.

In an embodiment, the first voltage source 201 and the second voltage source 211 vary with time. In a first sensing phase, the first voltage source 201 applies a first voltage to the first heating element 204, which causes the first heating element 204 to heat the first hotplate 208 to a first base temperature that has particular properties for sensing a gas of interest (e.g., CO2); and the second voltage source 211 applies a second voltage to the second heating element 214, which causes the second heating element 214 to heat the second hotplate 218 to a second base temperature that has particular properties for sensing the gas of interest. In a second sensing phase, the first voltage source 201 applies a third voltage to the first heating element 204, which causes the first heating element 204 to heat the first hotplate 208 to a third base temperature; and the second voltage source 211 applies a fourth voltage to the second heating element 214, which causes the second heating element 214 to heat the second hotplate 218 to a fourth base temperature. One of the first, second, third, and fourth base temperatures may be the ambient temperature. For example, the first base temperature may be 100° C., the second base temperature may be ambient temperature, the third base temperature may be 200° C., and the fourth base temperature may be 120° C. The first sensing phase and the second sensing phase each have particular properties for sensing a gas of interest (e.g., $CO_2$). Consequently, an output response of the gas of interest may be determined based on the respective changes of the voltage at output node 222 in the first sensing phase and the second sensing phase.

Figure 3B:
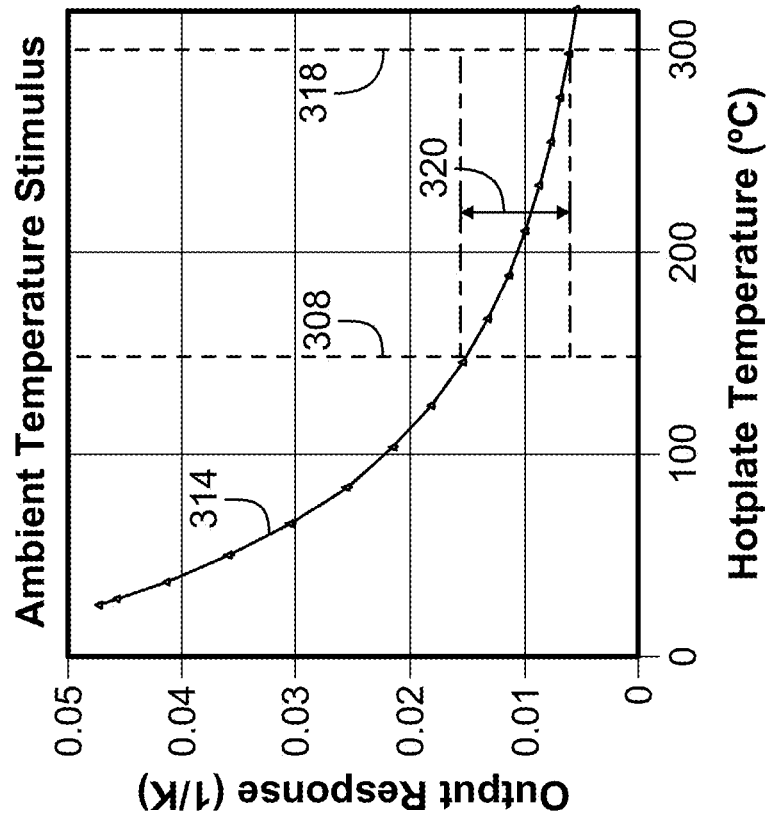
FIG. 3B shows an example diagram depicting an output response due to ambient temperature stimulus at different hotplate base temperatures in accordance with an embodiment of the present disclosure.
Figure 3A:
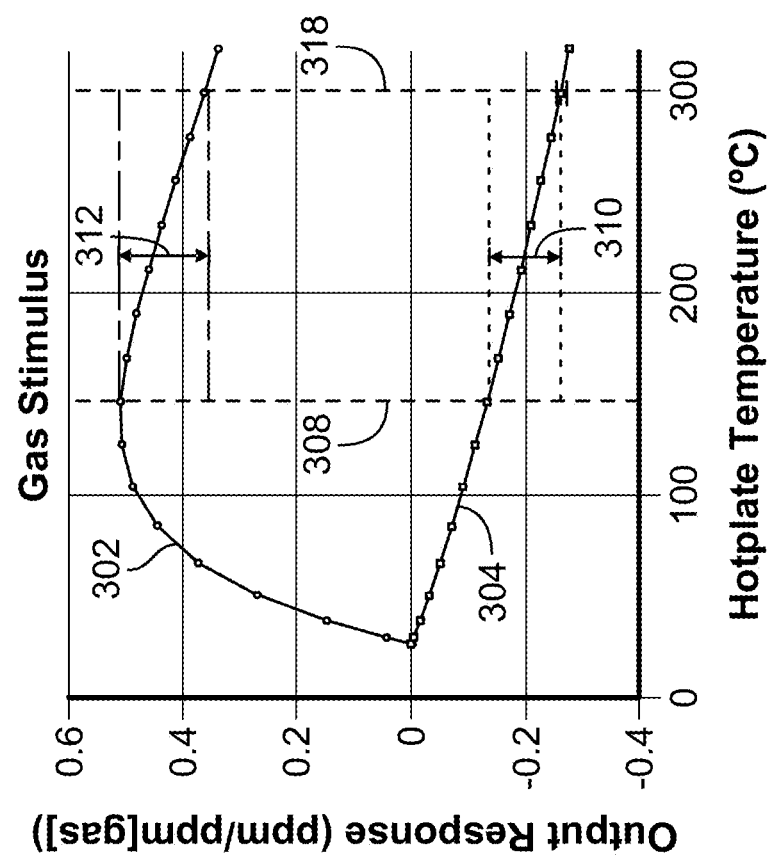
FIG. 3A shows an example diagram depicting an output response due to two different gas stimuli at different hotplate base temperatures in accordance with an embodiment of the present disclosure.

FIG. 3 shows an example diagram depicting an output response due to a stimulus at different hotplate base temperatures in accordance with an embodiment of the present disclosure, where the stimulus is defined as a gas concentration (in parts per million [ppm]) or ambient temperature change (in kelvins) and the output is defined as a change in voltage divider ratio (in parts per million). FIG. 3A shows an example graph of base Hotplate temperature (° C.) versus Output response that occurs when the air sample from air sample cavity 110, which may contain a gas of interest (e.g., $CO_2$) and a gas that is not of interest (e.g., $H_2O$), comes into contact with the first hotplate 208 at the first temperature (e.g., 150° C.) and the second gas sensor 218 at the second temperature (e.g., 300° C.). It will be understood that the output responses depend on properties of the sensing resistors, such as resistance at the respective base temperatures and variation of resistance with temperature. Although FIG. 3A depicts two measured gases, it will be understood that other gases may cause a response at the gas sensor device (e.g., at sensing resistors of the gas sensors). In addition, although FIG. 3A depicts the measurement of gases of the air sample at two particular hotplate temperatures, it will be understood that gases of the air sample may be measured at other suitable temperatures.

Output response to the gas of interest 302 represents the responsiveness of a gas sensor (e.g., corresponding to a degree of change in an output response at a voltage divider node) when heated to different base temperatures based on concentration of the gas of interest (e.g., carbon dioxide) taken from the air sample within air sample cavity 110 as a function of hotplate temperature, ° C. For example, processing circuitry may detect an output response of approximately 0.475-0.525 ppm at 150° C. hotplate temperature when the $CO_2$ concentration changes by 1 ppm. In accordance with the output response 302, an increase in concentration of carbon dioxide in the air sample may correspond to a decrease in the resistance of the first sensing resistor 206 and an increase in the divider voltage. In the context of the present disclosure, gas concentrations expressed in ppm refer to absolute gas concentration as a fraction of the whole, whereas output changes expressed in ppm or as dimensionless quantities refer to a voltage divider ratio, or equivalently, a voltage change as a fraction of a supply voltage.

Output response to the gas that is not of interest 304 represents the measured detection by processing circuitry of a concentration of a gas not of interest (e.g., water vapor) taken from the air sample within air sample cavity 110 as a function of hotplate temperature in ° C. For example, processing circuitry may detect an output response of approximately −0.13 to −0.15 ppm at 150° C. when the $H_2O$ concentration changes by 1 ppm. In some embodiments, an increase in concentration of water vapor in the air sample may correspond to an increase in the resistance of the first sensing resistor, and thus a decrease in the divider voltage.

First hotplate temperature 308 represents the first heating element 204 applying 150° C. base temperature to the first hotplate 208, including the first sensing resistor 206. First heating element 204 receives the first voltage from first heater voltage source $V_{H1}$ 201 and, as a result, applies the first base temperature, 150° C., to the first hotplate 208. First sensing resistor 206 receives the first base temperature from first heating element 204 and reacts by altering its resistance to a base resistance for the first sensing resistor 206. When in contact with the properties of the air sample (e.g., ambient temperature and concentration of $CO_2$ and $H_2O$), further changes in resistance of the first sensing resistor 206 contribute to changes in the voltage at output node 222.

Second hotplate temperature 318 represents the second heating element 214 applying 300° C. base temperature to the second hotplate 218, including the second sensing resistor 216. Second heating element 210 receives the second voltage from second heater voltage source $V_{H2}$ 211 and, as a result, applies the second base temperature, 300° C., to the second hotplate 218. Second sensing resistor 216 receives the second base temperature from second heating element 214 and reacts by altering its resistance to a second base resistance. When in contact with the properties of the air sample (e.g., ambient temperature and concentration of $CO_2$ and $H_2O$), further changes in resistance of the second sensing resistor 216 contribute to changes in the voltage at output node 222. As a result, the voltage at output node 222 changes based on the changing resistances of both sensing resistors, which in turn change based on the content of the gas and the respective response of the sensing resistors at particular temperatures.

Net output response to $H_2O$ 310 at first hotplate temperature 308 and second hotplate temperature 318 represents the net output response to concentration of $H_2O$ in the air sample from air sample cavity 110 when temperatures 308 and 318 are applied to hotplates 208 and 218. For example, 310 may represent the net of the first hotplate response of approximately −0.14 ppm/ppm[$H_2O$] at 150° C. and the second hotplate response of approximately −0.28 ppm/ppm [$H_2O$] at 300° C. The change of output voltage at output node 222 due to the concentration of $H_2O$ in the air sample equals the product of net output response to $H_2O$ 310 and voltage source $V_S$ 221.

Net output response to $CO_2$ 312 at first hotplate temperature 308 and second hotplate temperature 318 represents the net output response to concentration of $CO_2$ in the air sample from air sample cavity 110 when temperatures 308 and 318 are applied to hotplates 208 and 218. For example, 312 may represent the net of the first hotplate measurement of approximately 0.5 ppm/ppm[$CO_2$] at 150° C. and the second hotplate measurement of approximately 0.35 ppm/ppm [$CO_2$] at 300° C. The change of output voltage at output node 222 due to the concentration of $CO_2$ in the air sample equals the product of net output response to $CO_2$ 312 and voltage source $V_S$ 221.

FIG. 3B shows an example diagram depicting output response due to ambient temperature stimulus at different hotplate base temperatures in accordance with an embodiment of the present disclosure FIG. 3B shows an example graph of Hotplate base temperature (° C.) versus Output response (1/K) that occurs when the air sample from air sample cavity 110, at the ambient temperature, comes into contact with the first hotplate 208 at the first temperature (e.g., 150° C.) and the second hotplate 218 at the second temperature (e.g., 300° C.). It will be understood that the output responses depend on properties of the sensing resistors, such as resistance at the respective base temperatures and variation of resistance with temperature.

Output response at ambient temperature 314 represents the responsiveness of the gas sensor (e.g., corresponding to a degree of change in an output response at a voltage divider node), when heated to different base temperatures, to changes in the ambient temperature of the air sample. For example, the gas sensor may be more responsive to changes of the air sample in ambient temperature at lower hotplate temperatures (e.g., 150° C.) compared to higher hotplate temperatures (e.g., 300° C.). Although FIG. 3B depicts the degree of responsiveness to the air sample at ambient temperature for the first hotplate 208 at the first temperature and the second hotplate 218 at the second temperature, it will be understood that the sensors may be at any suitable temperature when measuring the air sample.

First hotplate temperature 308 represents the first heating element 204 applying 150° C. base temperature to the first hotplate 208, including the first sensing resistor 206. When in contact with the air sample, in addition to changes in resistance caused by concentration of $CO_2$ and $H_2O$, the ambient temperature will also modify the resistance of the sensing resistor 206 of the first hotplate 208. For example, the first hotplate 208 may detect an output response of approximately 0.015 (1/K) to changes in ambient temperature when set at a base temperature of 150° C.

Second hotplate temperature 318 represents second heating element 214 applying 300° C. base temperature of the second hotplate 218, including the second sensing resistor 216. When in contact with the air sample, in addition to changes in resistance caused by concentration of $CO_2$ and $H_2O$, the ambient temperature will also modify the resistance of the second sensing resistor 216 of the second hotplate 218. For example, the second hotplate 218 may detect an output response of approximately 0.005 (1/K) to changes in ambient temperature when set at a base temperature of 300° C.

Net output response to the air sample temperature 320 at first hotplate temperature 308 and second hotplate temperature 318 represents the net output response due to changes in the ambient temperature of the air sample when temperatures 308 and 318 are applied to hotplates 208 and 218. For example, 320 may represent the net of first hotplate response of approximately 0.015 (1/K) at 150° C. and second hotplate response of approximately 0.006 (1/K) at 300° C. Based on the known response of the sensing resistors to ambient temperature, $CO_2$ and $H_2O$ at different hotplate temperatures, and measurements made at different temperatures, e.g., 308 and 318, the concentration of the gas of interest (e.g., $CO_2$) may be estimated.

Figure 4:
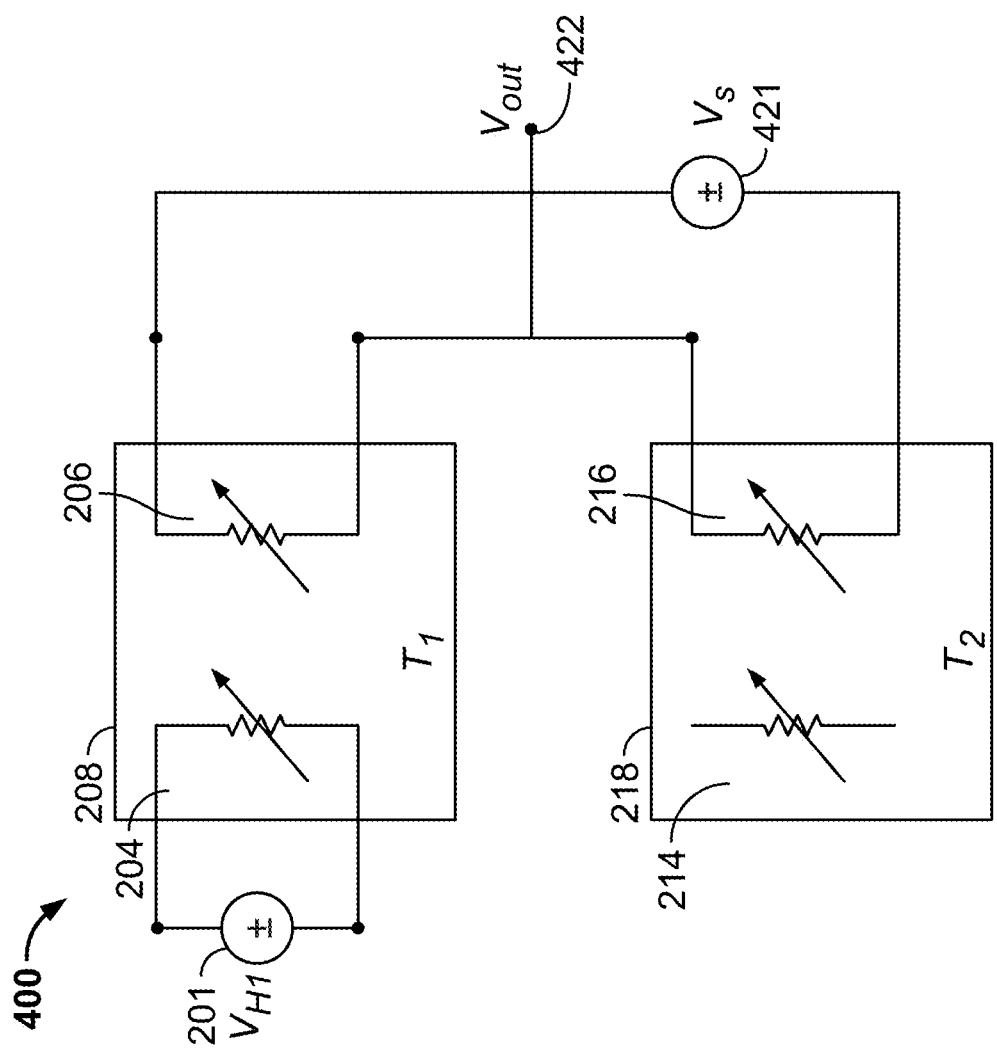
FIG. 4 shows an example circuit diagram of a gas sensor device including a first gas sensor at a controlled temperature and a second gas sensor at ambient temperature at in accordance with an embodiment of the present disclosure.

FIG. 4 shows an example circuit diagram of a gas sensor device including a first gas sensor at a controlled temperature and a second gas sensor at ambient temperature in accordance with an embodiment of the present disclosure. Although the circuit diagram of FIG. 4 includes particular circuit components, it will be understood that components may be substituted, modified, or changed in some embodiments. The exemplary gas sensor device incorporates a first hotplate 208, comprising a first heating element 204 and a first sensing resistor 206, and a second hotplate 218, including a disconnected second heating element 214 and a second sensing resistor 216. The gas sensor device of FIG. 4 further incorporates a first heater voltage source $V_{H1}$ 201 with respective nodes connected to the first heating element 204. It further incorporates a third voltage source $V_S$ 421, with respective nodes connected to the first sensing resistor 206 and the second sensing resistor 216, and measurement node 422, connected to the first sensing resistor 206 and the second sensing resistor 216.

First heater voltage source $V_{H1}$ 201 applies the first voltage to the first heating element 204, which causes the first heating element 204 to heat the first hotplate 208 to a first temperature that has particular properties for sensing a gas of interest (e.g., $CO_2$) of the air sample. For example, first heater voltage source $V_{H1}$ 201 may apply the first voltage resulting in the first heating element 204 generating a first base temperature of 100° C.

First sensing resistor 206 receives the first temperature from first heating element 204 and reacts by altering its resistance to a base resistance for sensing the air sample from air sample cavity 110. Subsequently, resistance of first sensing resistor 206 further changes based on properties of the air sample, including temperature and gas content (e.g., $CO_2$ and $H_2O$ content). For example, the first sensing resistor 206 may receive a base temperature of 100° C. from the first heating element 204 and change its resistance accordingly, establishing the base resistance for sensing the air sample, and change its resistance further according to the properties of the air sample (e.g., temperature and gas content). The first sensing resistor 206 in turn is in a series circuit with the second sensing resistor 216. The voltage at output node 422 varies based on the resistance values of the first sensing resistor 206 and the second sensing resistor 216 since the third voltage source $V_S$ 421 is constant.

Due to the absence of the second heater voltage source, second heating element 214 allows the second sensing resistor 216 to remain in thermal equilibrium with the air sample from air sample cavity 110. For example, the second sensing resistor 216 may experience an ambient temperature (e.g., 27° C. for an exemplary air sample) when in contact with the air sample.

Second sensing resistor 216 remains in thermal equilibrium with the air sample from air sample cavity 110. Subsequently, resistance of second sensing resistor 216 changes based on properties of the air sample, including temperature, which is ambient. For example, the second sensing resistor 216 may experience an ambient temperature of 27° C. when in contact with the air sample and change its resistance according to the temperature of the air sample (but not the gas content, due to the lack of heating). The resistance in turn is in a series circuit with the first sensing resistor 206. The voltage at output node 422 varies based on the resistance values of the first sensing resistor 206 and the second sensing resistor 216 since the voltage source $V_S$ 421 is constant.

Voltage source $V_S$ 421 supplies voltage to the series-connected first sensing resistor 206 and second sensing resistor 216. Output node 422 is a voltage divider based on voltage source $V_S$ 421, serving as a constant, and a ratio of the resistance of the first sensing resistor 206 and second sensing resistor 216. The resistance of first sensing resistor 206 initially changes to base resistance for sensing the air sample as a result of the first applied temperature by first heating element 204. Thereafter, resistance of first sensing resistor 206 changes again when in contact with the properties of the air sample (e.g., temperature and gas content of $CO_2$ and $H_2O$) from air sample cavity 110. The resistance of second sensing resistor 216 changes when in contact with the properties of the air sample (e.g., temperature) from air sample cavity 110, but remains independent of gas content in the air sample due to the lack of heating. So, the voltage at output node 422 changes according to changes in resistance of the first sensing resistor 206 and the second sensing resistor 216 based on their respective responses to the properties of the air sample. Consequently, an output response of a gas of interest (e.g., $CO_2$) can be determined based on the change in the voltage at output node 422.

Figure 5B:
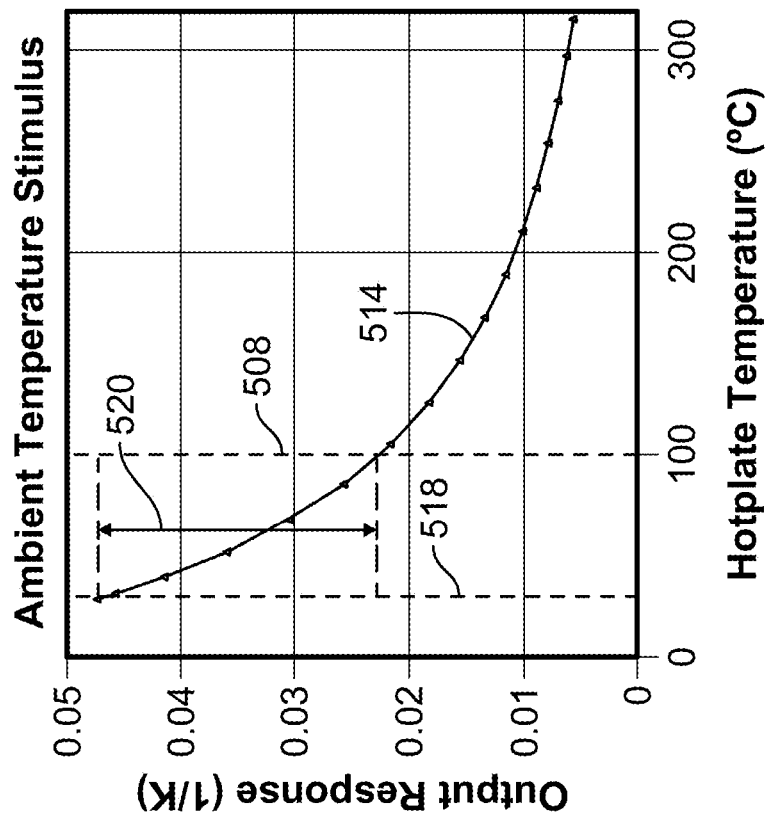
FIG. 5B shows an example diagram depicting an output response due to ambient temperature stimulus at different hotplate base temperatures in accordance with an embodiment of the present disclosure.
Figure 5A:
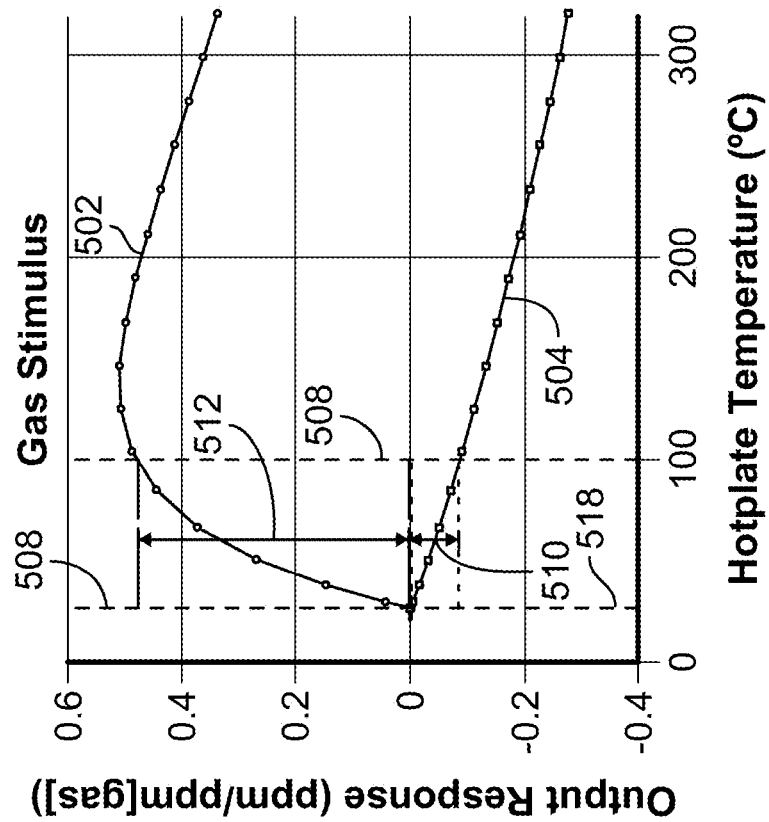
FIG. 5A shows an example diagram depicting an output response due to a gas stimulus at different hotplate base temperatures in accordance with an embodiment of the present disclosure.

FIG. 5A shows an example diagram depicting output response due to a gas stimulus at different hotplate base temperatures in accordance with an embodiment of the present disclosure, while FIG. 5B shows an example diagram depicting output response due to ambient temperature stimulus at different hotplate base temperatures in accordance with an embodiment of the present disclosure. FIG. 5A shows an example diagram of base Hotplate temperature (° C.) versus Output response that occurs when the air sample from air sample cavity 110, which may contain a gas of interest (e.g., $CO_2$) and a gas that is not of interest (e.g., $H_2O$), comes into contact with the first hotplate 208 at the first temperature (e.g., 100° C.) and the second hotplate 218 at the ambient temperature (e.g., 27° C.). It will be understood that the output responses depend on properties of the sensing resistors, such as resistance and variation of resistance with temperature. Although FIG. 5A depicts two measured gases, it will be understood that other suitable types or number of gases may be detected by the gas sensor device.

In addition, although FIGS. 5A and 5B depict the measurement of gases of the air sample at two particular hotplate base temperatures, it will be understood that gases of the air sample may be measured at a variety of suitable temperatures. For example, in an embodiment where second heating element 214 is selectively connected to a heating voltage source (not depicted in FIG. 4), the sensing resistors can be cycled through multiple different temperatures to create additional measurement points (e.g., each having known output responses to changes in $CO_2$, $H_2O$, and ambient temperature), such as setting the second temperature sensor to ambient first and then 150° C. second while setting the first temperature sensor to 100° C. first and 300° C. second. Other suitable numbers of temperature combinations may be utilized in other embodiments, providing additional data points for more accurately resolving the contribution of the gas of interest based on known respective responses at different temperatures.

In the embodiment depicted in FIG. 5A, output response to the gas of interest 502 represents the measured response at a voltage divider node to changes of concentration of carbon dioxide taken from the air sample within air sample cavity 110 as a function of hotplate temperature in ° C. For example, processing circuitry may detect an output response of approximately 0.46-0.52 ppm at 100° C. hotplate temperature when the $CO_2$ concentration changes by 1 ppm. At an ambient temperature the output response to the gas of interest may be essentially zero. In an embodiment, an increase in concentration of carbon dioxide in the air sample may correspond to a decrease in the resistance of the first sensing resistor 206 while the second sensing resistor 216 is relatively non-responsive.

Output response to the gas that is not of interest 504 represents the measured response of a voltage divider node to changes of concentration of water vapor taken from the air sample within air sample cavity 110 as a function of hotplate temperature in ° C. For example, processing circuitry may detect an output response of approximately −0.08 ppm at 100° C. hotplate temperature when the $H_2O$ concentration changes by 1 ppm. At an ambient temperature the output response to the water vapor may be essentially zero. In some embodiments, an increase in concentration of water vapor in the air sample may correspond to an increase in the resistance of the first sensing resistor 206 while the second sensing resistor 216 is non-responsive.

First sensor hotplate temperature 508 represents the first heating element 204 applying a 100° C. base temperature to the first hotplate 208, including the first sensing resistor 206. First heating element 204 receives the first voltage from first heater voltage source $V_{H1}$ 201 and, as a result, applies the first temperature, 100° C., to the first hotplate 208. First sensing resistor 206 receives the first temperature from first heating element 204 and reacts by altering its resistance to the base resistance for sensing the air sample from air sample cavity 110. When in contact with the properties of the air sample (e.g., temperature and concentration of $CO_2$ and $H_2O$), further changes in resistance of the first sensing resistor 206 contribute to changes in the voltage at output node 422 (e.g., along with changes to second sensing resistor 216).

Second sensor hotplate temperature 518 represents the second hotplate 218, including the second sensing resistor 216, experiencing the ambient temperature (e.g., 27° C.) when in contact with the air sample from air sample cavity 110. Since there's no second heater voltage source, and consequently no second heating element (or a disconnected heating element), the resistance of the second sensing resistor 216 is independent of gas (e.g., $CO_2$ and $H_2O$) in the air sample. For example, as depicted by FIG. 5A, the second hotplate 218 reads an output response of approximately 0.0 ppm per 1 ppm change in either $CO_2$ or $H_2O$. When in contact with the properties of the air sample (e.g., temperature), changes in resistance of the second sensing resistor 216 contribute to changes in the voltage at output node 422.

A net output response for the gas that is not of interest 510 at second hotplate temperature 518 and first hotplate temperature 508 represents the net output response for concentration of the gas that is not of interest (e.g., $H_2O$) in the air sample from air sample cavity 110 when temperatures 508 and 518 are applied to hotplates 208 and 218. For example, 510 may represent the net of the first hotplate response of approximately −0.08 ppm/ppm[$H_2O$] at 100° C. and the second hotplate response of approximately 0.0 ppm/ppm [$H_2O$] at 27° C. The change of the voltage at output node 222 due to the concentration of $H_2O$ in the air sample equals the product of net output response for $H_2O$ 510 and voltage source $V_S$ 221.

A net output response for the gas of interest 512 at first hotplate temperature 508 and second hotplate temperature 518 represents the net output response for concentration of the gas of interest (e.g., $CO_2$) in the air sample from air sample cavity 110 when temperatures 508 and 518 are applied to hotplates 208 and 218. For example, 512 may represent the net of the first hotplate measurement of approximately 0.48 ppm/ppm[$CO_2$] at 100° C. and the second hotplate measurement of approximately 0.0 ppm/ppm[$CO_2$] at 27° C. The change of the voltage at output node 222 due to the concentration of $CO_2$ in the air sample equals the product of net output response for $CO_2$ 512 and voltage source $V_S$ 221.

FIG. 5B shows an example graph of Hotplate temperature (° C.) versus Output response (1/K) that depicts detected ambient temperature stimulus of the air sample when in contact with the first hotplate 208 at the first temperature (e.g., 100° C.) and the second hotplate 218 at the second temperature (e.g., 27° C.). Although FIG. 5B depicts the degree of responsiveness to the air sample at ambient temperature for the first hotplate 208 at the first temperature and the second hotplate 218 at the second temperature, it will be understood that the sensors may be at any suitable temperature when measuring the air sample as described herein.

Output response at ambient temperature 514 represents the degree of responsiveness at a voltage divider node to changes in the air sample temperature. For example, the gas sensor may be more responsive to changes of the air sample temperature at lower hotplate temperatures (e.g., 27° C.) compared to higher hotplate temperatures (e.g., 100° C.).

First hotplate temperature 508 represents the first heating element 204 applying a 100° C. base temperature to the first hotplate 208, including the first resistor 206. Further changes in resistance of the first sensing resistor 206, according to the properties of the air sample (e.g., temperature and concentration of $CO_2$ and $H_2O$), contribute to changes in the voltage at output node 422. Consequently, an output response can be determined based on the changes in the voltage at output node 422. For example, the first hotplate 208 may detect an output response of approximately 0.023 (1/K) to changes in ambient temperature when set at a base temperature of 100° C.

Second hotplate temperature 518 represents the second hotplate 218 receiving the ambient temperature from the air sample. Due to the absence of a second heater voltage source, and consequently no second heating element (or a disconnected heating element), the resistance of the second sensing resistor 216 changes according to temperature, contributing to changes in the voltage at output node 422. Consequently, an output response can be determined based on the changes in the voltage at output node 422. For example, the second hotplate 218 may detect an output response of approximately 0.047 (1/K) to changes in ambient temperature when starting from an ambient base temperature of 27° C.

A net of output response for the air sample at ambient temperature 520 at second hotplate temperature 518 and first hotplate temperature 516 represents the net output response for changes in the properties of the air sample when temperatures 508 and 518 are applied to hotplates 508 and 518. For example, 520 may represent the difference of second sensor measurement of approximately 0.047 (1/K) at 27° C. and first sensor measurement of approximately 0.023 (1/K) at 100° C.

Figure 6:
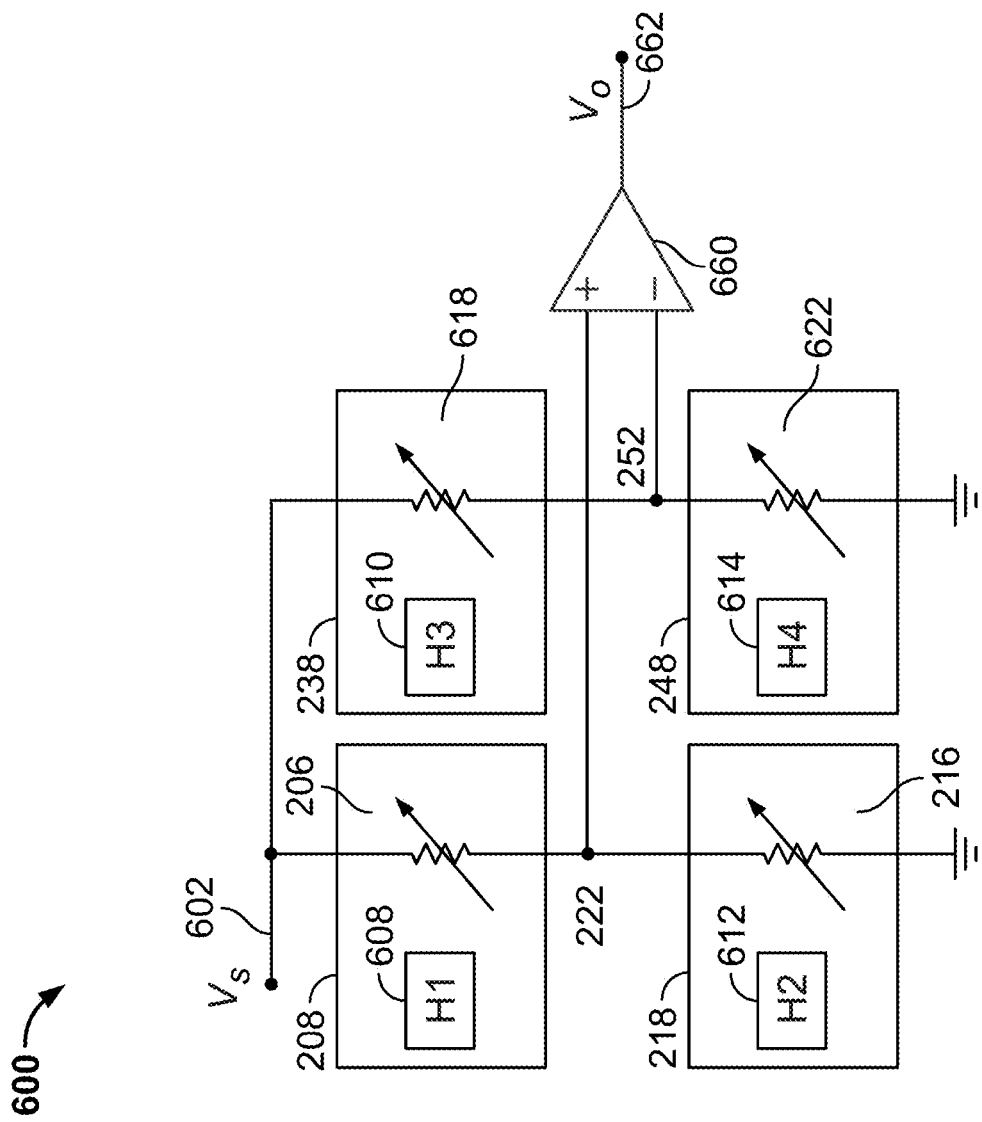
FIG. 6 shows an example circuit diagram of a gas sensor device including four gas sensors in accordance with an embodiment of the present disclosure.

FIG. 6 shows an example circuit diagram of a gas sensor device including four gas sensors in accordance with some embodiments of the present disclosure. For simplicity, the heater voltage sources and heating elements previously described have been generically described as "heaters" 608, 610, 612, and 614, and it will be understood that each heater includes appropriate circuitry for heating a respective hotplate, such as a heater voltage source and a heating element. Example circuitry includes the first sensing resistor 206 in series with the second sensing resistor 216, and the third sensing resistor 618 in series with the fourth sensing resistor 622. In addition, the circuitry includes the voltage source $V_S$ 602, node 222, node 252, differential amplifier 660, and output node 662. Although the diagram includes particular circuit components, it will be understood that components may be substituted, modified, or changed in some embodiments. Voltage source $V_S$ 602 connects to a first node of sensing resistor 206 and a first node of sensing resistor 618, node 222 connects to a second node of sensing resistor 206 and a first node of second resistor 216, node 252 connects to a second node of sensing resistor 618 and a first node of second resistor 622, nodes 222 and 252 connect to inputs of differential amplifier 660, and a second node of each of sensing resistor 216 and sensing resistor 622 connects to ground.

First heater 608 heats the first hotplate 208, including the first sensing resistor 206, to a first temperature that has particular properties for sensing a gas of interest (e.g., $CO_2$) of the air sample. For example, the first heater 608 may generate a base temperature of 100° C. for hotplate 208.

First sensing resistor 206 receives the first temperature from first heater 608 and reacts by altering its resistance to a base resistance for sensing the air sample from air sample cavity 110. Subsequently, resistance of first sensing resistor 206 further changes based on properties of the air sample, including temperature and gas content (e.g., $CO_2$ and $H_2O$ content). For example, the first sensing resistor 206 may receive a base temperature of 100° C. from the first heater 608, change its resistance accordingly, establishing the base resistance for sensing the air sample, and change its resistance further according to the properties of the air sample. The first sensing resistor 206 in turn is in a series circuit with the second sensing resistor 216. The voltage at input node 222 of differential amplifier 660 varies based on the resistance values of the first sensing resistor 206 and the second sensing resistor 216 since the voltage source $V_S$ 602 is constant.

In an embodiment, the second heater 612 may be inactive or absent such that the second sensing resistor 216 is allowed to remain in thermal equilibrium with the air sample from air sample cavity 110. For example, the second sensing resistor 216 may experience an ambient temperature (e.g., 27° C.) when in contact with the air sample from air sample cavity 110. When in contact with the air sample, the gas sensor device measures an output response of ambient temperature stimulus (e.g., the degree of responsiveness of the gas sensor device to changes in the air sample at ambient temperature). For example, the second sensing resistor 216 may experience an ambient temperature of 27° C. when in contact with the air sample from air sample cavity 110 and change its resistance due to the properties of the air sample (e.g., temperature), but not based on the gas content as described herein. The resistance in turn is in a series circuit with the first sensing resistor 206 and in turn influences the voltage at input node 222 to differential amplifier 660.

Third heater 610 heats the third hotplate 238, including the third sensing resistor 618, to a third temperature that has particular properties for sensing a gas of interest (e.g., $CO_2$) of the air sample. For example, the third heater 610 may generate a base temperature for the third hotplate 238. Although the third base temperature may be different than the other base temperatures for the other hotplates of FIG. 6, in an embodiment the base temperature may be 120° C. for the hotplate 238, i.e. such that the third base temperature of third hotplate 238 may equal the base temperature of hotplate 208. The third sensing resistor 618 in turn is in a series circuit with the fourth resistor 622. The voltage at input node 252 of differential amplifier 660 varies based on the resistance values of the third sensing resistor 618 and the fourth sensing resistor 622 since the voltage source $V_S$ 602 is constant.

Fourth heater 614 heats the fourth hotplate 248, including the fourth sensing resistor 622, to a fourth temperature that has particular properties for sensing a gas of interest (e.g., $CO_2$) of the air sample. For example, the fourth heater 614 may generate a base temperature for sensing resistor 622 that is relatively higher than the other applied temperatures and where the $CO_2$ response is still large (e.g., 180° C.). Fourth sensing resistor 622 thus is heated to the fourth temperature and alters its resistance to a base resistance for sensing the air sample. Subsequently, the resistance of fourth sensing resistor 622 further changes based on properties of the air sample from air sample cavity 110, including temperature and gas content (e.g., $CO_2$ and $H_2O$ content). The fourth sensing resistor 622 in turn is in a series circuit with the third sensing resistor 618, thus impacting the voltage at input node 252 of differential amplifier 660.

Differential amplifier 660 takes the difference of the voltage at the first measurement node 222 and the voltage at the second measurement node 252 and amplifies the difference. Measurement node 222 connects between the first sensing resistor 206 and the second sensing resistor 216, while measurement node 252 connects between the third sensing resistor 618 and the fourth sensing resistor 622. In some embodiments, the differential amplifier 660 may subtract the voltage at measurement node 252, $V_B$, from the voltage at measurement node 222, $V_A$, and amplify the difference according to a gain of the differential amplifier to generate the output voltage $V_o$ 662.

It will be recognized that the structures recited above form a resistive bridge. In the embodiment shown, the differential amplifier 660 computes the output voltage $V_o$ 662, which is proportional to the difference of the voltages at the two measurement nodes 222 and 252. Although a differential amplifier is depicted, it will be apparent that other means of computation may be suitable, such as a microcontroller unit (MCU). Furthermore, although subtraction is depicted, other arithmetic functions may be suitable. For instance, in some embodiments, the differential amplifier 660 may multiply the voltage at node 222 by a first gain and the voltage at node 252 by a second gain, where the first gain and the second gain are unequal. In a further embodiment, the first gain may have a first temperature dependence and the second gain may have a second temperature dependence, wherein the first temperature dependence may be unequal to the second temperature dependence. The gas sensor device may further comprise digital circuits (e.g., analog-to-digital converters, multipliers and adders), and temperature sensors (e.g., bandgap references or resistive temperature detectors), not shown in FIG. 6.

Figure 7B:
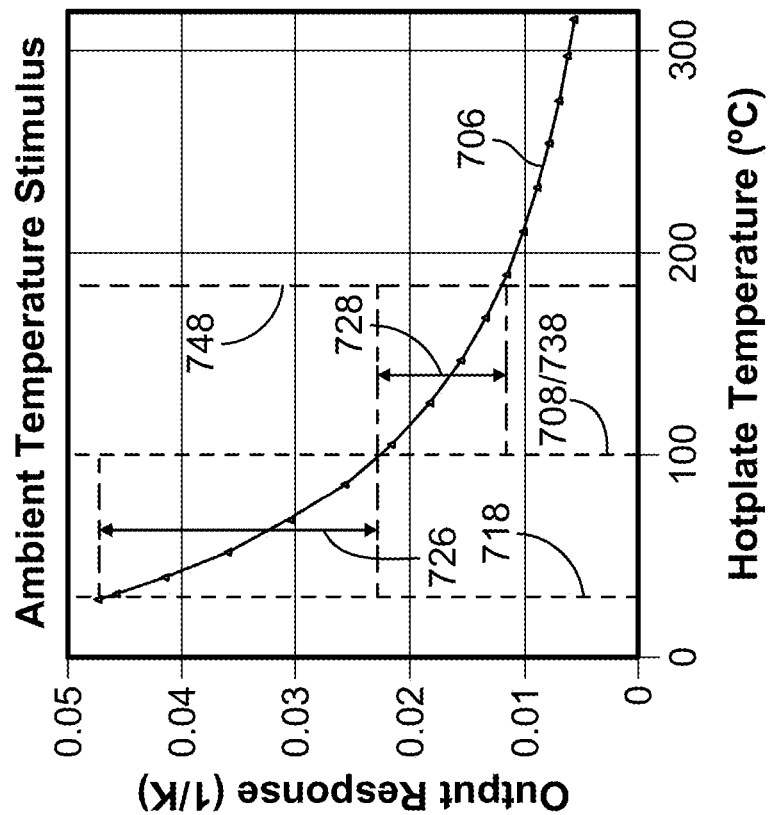
FIG. 7B shows an example diagram depicting an output response due to ambient temperature stimulus at different hotplate base temperatures in accordance with an embodiment of the present disclosure.
Figure 7A:
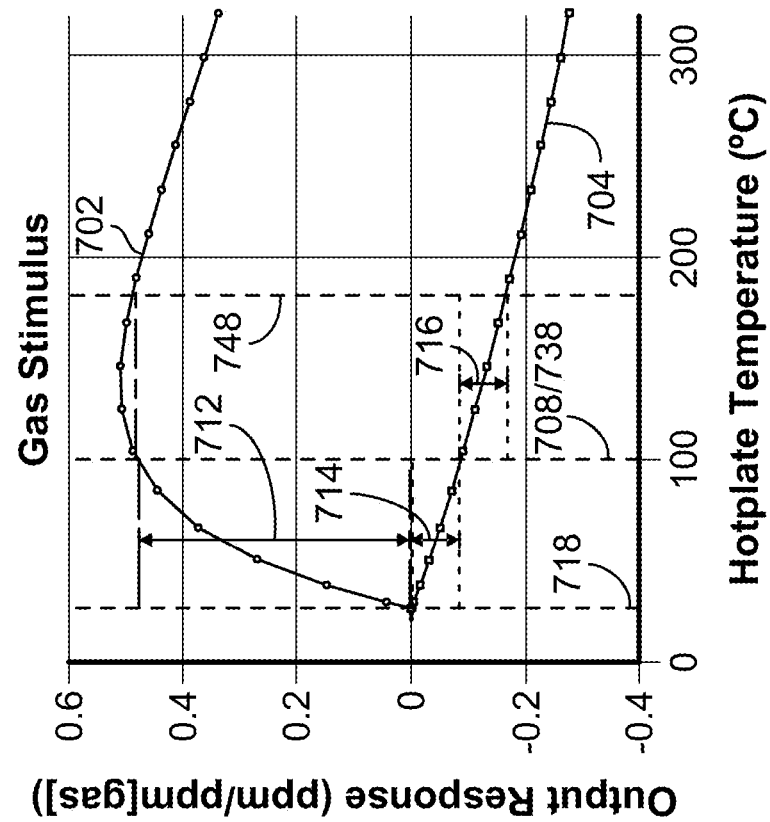
FIG. 7A shows an example diagram depicting an output response due to a gas stimulus at different hotplate base temperatures in accordance with an embodiment of the present disclosure.

FIG. 7A shows an example diagram depicting output response due to a gas stimulus at different hotplate base temperatures while FIG. 7B shows an example diagram depicting output response due to ambient temperature stimulus at different hotplate base temperatures, in accordance with an embodiment of the present disclosure (e.g., for the configuration of FIG. 6). FIG. 7A shows an example graph of base Hotplate temperature (° C.) versus Output response that occurs when the air sample from air sample cavity 110, which may contain a gas of interest (e.g., $CO_2$) and a gas that is not of interest (e.g., $H_2O$), comes into contact with the first hotplate 208 at the first temperature (e.g., 100° C.), the second hotplate 218 at the ambient temperature (e.g., 27° C.), the third hotplate 238 at the third temperature (e.g., 100° C.), and the fourth hotplate 248 at the fourth temperature (e.g., 180° C.). It will be understood that the output responses depend on properties of the sensing resistors, such as resistance at the respective base temperatures and variation of resistance with temperature. Although FIG. 7A depicts two measured gases, it will be understood that other suitable number and types of gases may be detected by the gas sensor device. In addition, although FIG. 7A depicts the measurement of gases of the air sample at three hotplate temperatures, it will be understood that gases of the air sample may be measured at a variety of suitable temperatures. In some embodiments, the measurements described for FIGS. 7A and 7B may be carried out by two hotplates (e.g., the configuration of FIG. 2), by iteratively cycling through different temperatures as described herein.

Output response to the gas of interest 702 represents the measured response at a voltage divider node based on a concentration of the gas of interest (e.g., carbon dioxide) taken from the air sample within air sample cavity 110 when sensors are heated to different base temperatures as a function of hotplate temperature, in ° C. For example, processing circuitry may detect an output response of approximately 0.48 ppm at a 100° C. hotplate temperature when the $CO_2$ concentration changes by 1 ppm. In some embodiments, an increase in concentration of carbon dioxide in the air sample may correspond to a decrease in the resistance of the first sensing resistor 206. Output response for the gas that is not of interest 704 represents the measured change in resistance due to a gas that is not of interest (e.g., water vapor) taken from the air sample within air sample cavity 110 as a function of hotplate temperature, in ° C. For example, processing circuitry may detect an output response of approximately −0.08 ppm at 100° C. hotplate temperature when the $H_2O$ concentration changes by 1 ppm. In some embodiments, an increase in concentration of water vapor in the air sample may correspond to an increase in the resistance of the first sensing resistor.

First hotplate temperature 708 represents the first heater 608 applying 100° C. to the first hotplate 208, including the first sensing resistor 206. First sensing resistor 206 is heated to the first temperature by heater 608 and reacts by altering its resistance to the base resistance for first sensing resistor 206. When in contact with the properties of the air sample (e.g., temperature and concentration of $CO_2$ and $H_2O$), first sensing resistor further changes its resistance to contribute to changes in output voltage $V_o$ 662.

Second hotplate temperature 718 represents the second hotplate 218, including the second sensing resistor 216, experiencing the ambient temperature of 27° C. when in contact with the air sample from air sample cavity 110. Since there's no heating of the second sensing resistor 216 in the depicted embodiment, the response is independent of gas (e.g., $CO_2$ and $H_2O$) in the air sample. For example, as depicted by FIG. 7A, the second hotplate 218 reads an output response of approximately 0.0 ppm/ppm[$CO_2$] and 0.0 ppm/ppm[$H_2O$] at ambient temperature.

Third hotplate temperature 738 represents the third heater 610 applying 100° C. to the third hotplate 238, including the third sensing resistor 618. Third sensing resistor 618 receives the third temperature from third heater 610 and reacts by altering its resistance to the base resistance for third sensing resistor 618. When in contact with the properties of the air sample (e.g., temperature and concentration of $CO_2$ and $H_2O$), further changes in resistance of the third sensing resistor 618 to contribute to changes in output voltage $V_o$ 662.

Fourth hotplate temperature 748 represents the fourth heater 614 applying 180° C. to the fourth hotplate 248, including the fourth sensing resistor 622. Fourth sensing resistor 622 receives the fourth temperature from fourth heater 614 and reacts by altering its resistance to the base resistance the fourth sensing resistor 622. When in contact with the properties of the air sample (e.g., temperature and concentration of $CO_2$ and $H_2O$), further changes in resistance of the fourth sensing resistor 622 contribute to changes in output voltage $V_o$ 662.

A net output response for $CO_2$ 712 at first hotplate temperature 708 and second hotplate temperature 718 represents the net output response to concentration of $CO_2$ in the air sample from air sample cavity 110 when temperatures 708 and 718 are applied/received at hotplates 208 and 218. For example, 712 may represent the net of the first hotplate response of approximately 0.48 ppm/ppm[$CO_2$] at 100° C. and the second hotplate response of approximately 0.0 ppm/ppm[$CO_2$] at 27° C. In the embodiment of FIG. 7A, the net output response to $CO_2$ at the third temperature 738 and the fourth temperature 748 may be minimal, with both associated hotplates and sensing resistors (e.g., third sensing resistor 618 and fourth sensing resistor 622) having been set at temperatures where their response to $CO_2$ is substantially identical but the response to $H_2O$ is different.

A net of output response for $H_2O$ 714 at second hotplate temperature 718 and first hotplate temperature 708 represents the net output response to concentration of $H_2O$ in the air sample from air sample cavity when temperatures 708 and 718 are applied/received at hotplates 208 and 218. For example, 714 may represent the net of the second sensor measurement of approximately 0.0 ppm/ppm[$H_2O$] at 27° C. and the first sensor measurement of approximately −0.08 ppm/ppm[$H_2O$] at 100° C.

A net of output response for $H_2O$ 716 at fourth hotplate temperature 748 and third hotplate temperature 738 represents the difference of output response to concentration of $H_2O$ in the air sample from air sample cavity 110 when temperatures 738 and 748 are applied/received at hotplates 238 and 248. For example, 716 may represent the difference of the third hotplate response of approximately −0.08 ppm/ppm[$H_2O$] at 100° C. and the fourth hotplate response of approximately −0.16 ppm/ppm[$H_2O$] at ~180° C. In this manner, the differences in output 716 and 714 for $H_2O$ may be substantially identical (e.g. −0.08 ppm/ppm[$H_2O$]) such that the effect of $H_2O$ cancels in the outputs of the respective voltage dividers.

FIG. 7B shows an example graph of Hotplate temperature (° C.) versus Output response (1/K) that depicts detected ambient temperature stimulus of the air sample when in contact with the first hotplate 208 at the first temperature (e.g., 100° C.), the second hotplate 218 at the ambient temperature (e.g., 27° C.), the third hotplate 238 at the third temperature (e.g., 100° C.), and the fourth hotplate 248 at the third temperature (e.g., 180° C.).

An output response at ambient temperature 706 represents the responsiveness of the gas sensor device, including processing circuitry, the first hotplate 208, the second hotplate 218, the third hotplate 238, and the fourth hotplate 248, to changes of the ambient temperature of the air sample. For example, the gas sensor device may be more responsive to changes of the air sample in ambient temperature at lower hotplate temperatures (e.g., 27° C.) compared to higher hotplate temperatures (e.g., —180° C.).

First hotplate temperature 708 and third hotplate temperature 738 represent the first heater 608 and third heater 610 applying a 100° C. base temperature to the first hotplate 208 and third hotplate 238, respectively. When in contact with the properties of the air sample (e.g., temperature and concentration of $CO_2$ and $H_2O$), changes in resistance of the sensing resistors contribute to changes in output voltage $V_o$ 662. For example, the first hotplate 208 and third hotplate 238 may have an output response of approximately 0.023 (1/K) to changes in ambient temperature when set at a base temperature of 100° C.

Second hotplate temperature 718 represents second heater 612 being absent, off, or disconnected such that the second hotplate 218 has a base temperature corresponding to the ambient temperature (e.g., 27° C.). When in contact with the properties of the air sample (e.g., temperature), changes in resistance of the second sensing resistor 216 contribute to changes in output voltage $V_o$ 662. For example, the second hotplate 218 may have an output response of approximately 0.047 (1/K) to changes in ambient temperature when set at a base ambient temperature of 27° C.

Fourth hotplate temperature 738 represents third heater 614 applying a ~180° C. base temperature to hotplate 248. When in contact with the properties of the air sample (e.g., temperature and concentration of $CO_2$ and $H_2O$), further changes in resistance of the fourth sensing resistor 622 contribute to changes in output voltage $V_o$ 662. For example, the fourth hotplate 238 may have an output response of approximately 0.012 (1/K) to changes in ambient temperature when set at a base temperature of at ~180° C.

A net output response 726 for the air sample at first hotplate temperature 708 and second hotplate temperature 718 represents the net output response due to changes in the properties of the air sample when the temperatures 708 and 718 are applied/received at hotplates 208 and 218 For example, 726 may represent the difference of second sensor measurement of approximately 0.047 (1/K) at 27° C. and first sensor measurement of approximately 0.023 (1/K) at 100° C.

A net output response 728 for the air sample at fourth hotplate temperature 748 and third hotplate temperature 738 represents the net changes in the properties of the air sample when temperatures 738 and 748 are applied to hotplates 238 and 248, respectively. For example, 728 may represent the difference between the third sensor measurement of approximately 0.023 (1/K) at 100° C. and the fourth sensor measurement of approximately 0.012 (1/K) at ~180° C.

By applying suitable base temperature values (e.g., including ambient temperature) to respective sensing resistors and configuring the sensing resistors appropriately (e.g., as depicted in FIG. 6), the change in resistances due to carbon dioxide can be distinguished from changes due to temperature and water vapor. It will be understood that different sensors (e.g., sensing resistors having different responses to gases of interest, temperature, etc.) may have different output response patterns, which will result in different selections of respective heating temperatures. However, in the embodiment of FIGS. 6-7, the respective temperatures applied to the first and second sensing resistors are such that the output responses to water vapor of the respective resistor dividers cancel and a substantial carbon dioxide response is established between first and second sensing resistors.

Figure 8:
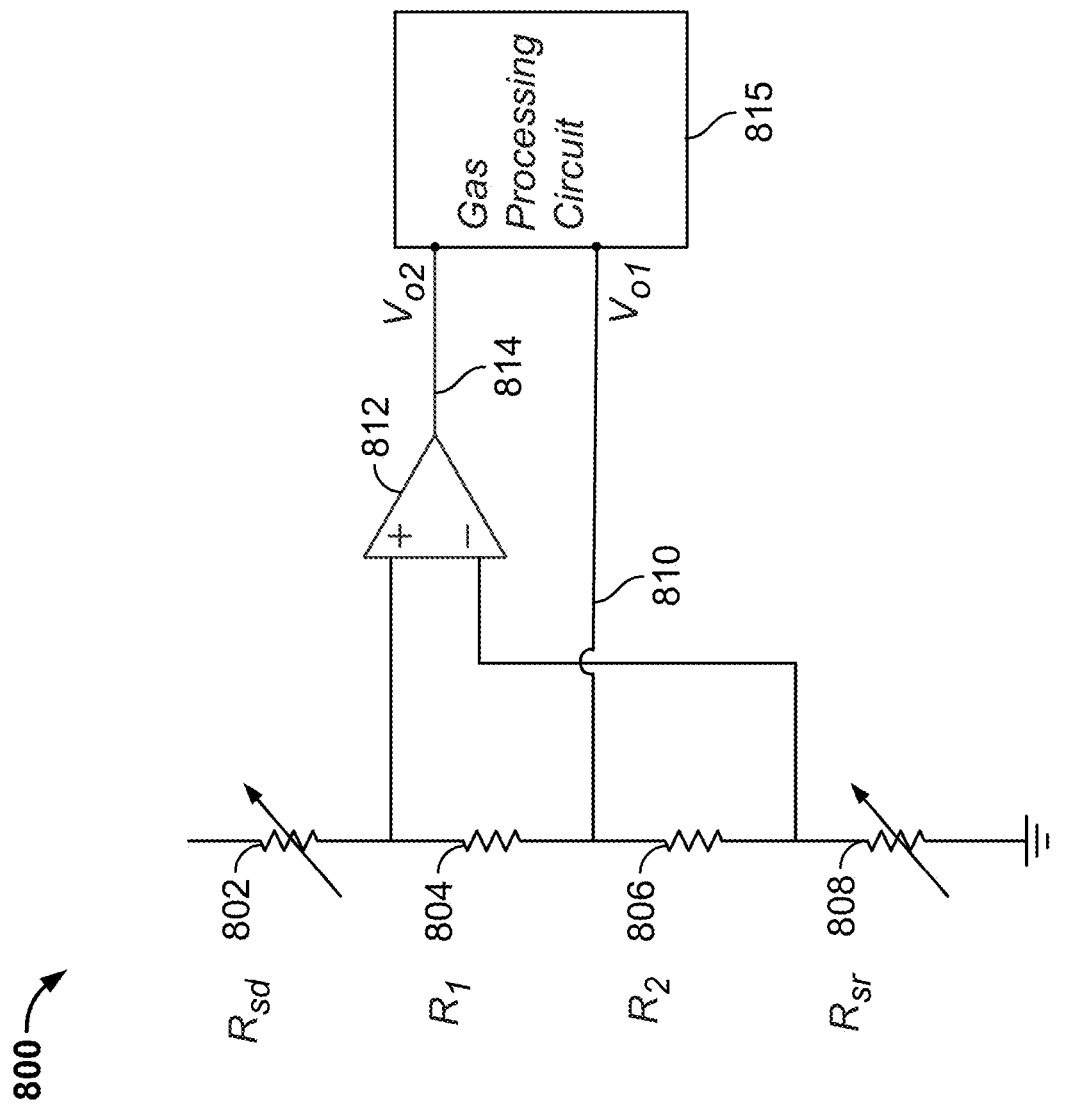
FIG. 8 shows an example circuit diagram of a gas sensor device including gas sensors with sensing resistors and one or more fixed resistors in accordance with an embodiment of the present disclosure.

FIG. 8 shows an example circuit diagram of gas sensor device including gas sensors with a first sensing resistor 802, a first fixed resistor 804, a second fixed resistor 806, and a second sensing resistor 808. The example circuit also includes differential amplifier 812. In the context of the present disclosure, a fixed resistor is any ordinary, unheated resistor, such as a metal film resistor in an integrated circuit chip, whereas a sensing resistor, such as the second resistor 106 of FIG. 1 or the second resistor 216 of FIG. 2, is a resistor configured to receive a base temperature from a heating element and vary its resistance according to a variation of hotplate temperature according to a property of an air sample. A sensing resistor may comprise materials selected for a suitable temperature-resistivity characteristic, such as high resistivity at the base temperature, linear response, or large variability of resistivity with respect to temperature. A fixed resistor may comprise materials selected for a suitable temperature-resistivity characteristic that gives a suitable response of the first output voltage Vo1 810 and the second output voltage Vo2 814 with respect to ambient temperature, such as a small variability of resistivity with respect to temperature. In the embodiment of FIG. 8, although not depicted, one or both of sensing resistor 802 and sensing resistor 808 may be associated with respective heating elements and voltage sources to control those heating elements. Further, although the diagram and following description includes particular circuit components, it will be understood that components may be substituted, modified, or changed in some embodiments. For example, although two fixed resistors are depicted and described in FIG. 8, along with measurement nodes associated with those fixed resistors, in other embodiments different numbers of fixed resistors (e.g., one, three, etc.) and measurement nodes may be utilized.

First sensing resistor 802 receives a first temperature from the first heating element (not shown) and reacts by altering its resistance to a base resistance for sensing the air sample from air sample cavity 110. Subsequently, resistance of first sensing resistor 802 further changes based on properties of the air sample, including temperature and gas content (e.g., $CO_2$ and $H_2O$ content). For example, the first sensing resistor 802 may receive 150° C. from the first heating element, change its resistance accordingly, establishing the base resistance for sensing the air sample, and change its resistance further according to the properties of the air sample. The first sensing resistor 802 in turn is in a series circuit with the first fixed resistor 804 at a first node, which also connects to the positive input of differential amplifier 812.

The first fixed resistor 804 provides a consistent (e.g., minimally varying with ambient temperature) resistance to the circuit and connects, at the first node, in series with the first sensing resistor 802. The first fixed resistor 804 further connects in series to the second fixed resistor 806 at a second node, which concurrently feeds to the first output voltage $V_{o1}$ 810. The second fixed resistor 806 provides a consistent resistance within the series circuit and connects in series to the second sensing resistor 808 at a third node, which feeds into the negative input of differential amplifier 812, which produces output voltage $V_{o2}$ 814. In some embodiments, the first and second fixed resistors may have resistances substantially small (e.g., 10%) compared to the base resistances of the first and sensing resistors. Consequently, the first fixed resistor 804, the second fixed resistor 806, and the differential amplifier 812 may function as a current sensor.

Second sensing resistor 808 receives the second temperature from the second heating element and reacts by altering its resistance to a base resistance for sensing the air sample. Subsequently, resistance of second sensing resistor 808 further changes based on properties of the air sample from air sample cavity 110, including temperature and gas content (e.g., $CO_2$ and $H_2O$ content). For example, the second sensing resistor 808 may receive 300° C. from the second heating element, change its resistance accordingly, establishing the base resistance for sensing the air sample, and change its resistance further when in contact with the air sample from air sample cavity 110. First output voltage $V_{o1}$ 810 is generated by the voltage divider between, in the first instance, the series combination of the first sensing resistor 802 and the first fixed resistor 804, and in the second instance, the series combination of the second fixed resistor 806 and the second sensing resistor 808. Any changes in output voltage $V_{o1}$ 810 will be in response to changes in the ratio of the resistance of the first sensing resistor and the second sensing resistor. The current, in turn, is representative of an overall resistance of all of the resistors. In this manner, the relative difference between the sensing resistors (represented by output voltage $V_{o1}$ 810) and total values of the sensing resistors (represented by output voltage $V_{o2}$ 814) may be determined, to more accurately calculate the contribution of the gas of interest to the changes in resistance of the sensing resistors (e.g., based on known output responses at particular temperatures, as described herein).

Gas processing circuit 815 computes the output voltage 817 as a function of output voltage $V_{o1}$ 810 and output voltage $V_{o2}$ 812. Gas processing circuit 815 may include any suitable combination of circuits, such as amplifiers, analog-to-digital converters, and digital arithmetic circuits. In an embodiment, the gas processing circuit 815 may compute the sum of output voltage $V_{o1}$ 810 and output voltage $V_{o2}$ 812. In another embodiment, the gas processing circuit 815 may compute the sum of output voltage $V_{o1}$ 810 multiplied by a first gain and output voltage $V_{o2}$ 812 multiplied by a second gain, wherein the first gain may be unequal to the second gain. In an embodiment, either the first factor or the second factor may depend on ambient temperature, wherein the ambient temperature may be determined by a suitable temperature sensor. The processing circuitry may comprise analog circuits (e.g., amplifiers), digital circuits (e.g., analog-to-digital converters, multipliers and adders), and temperature sensors (e.g., bandgap references or resistive temperature detectors).

Figure 9:
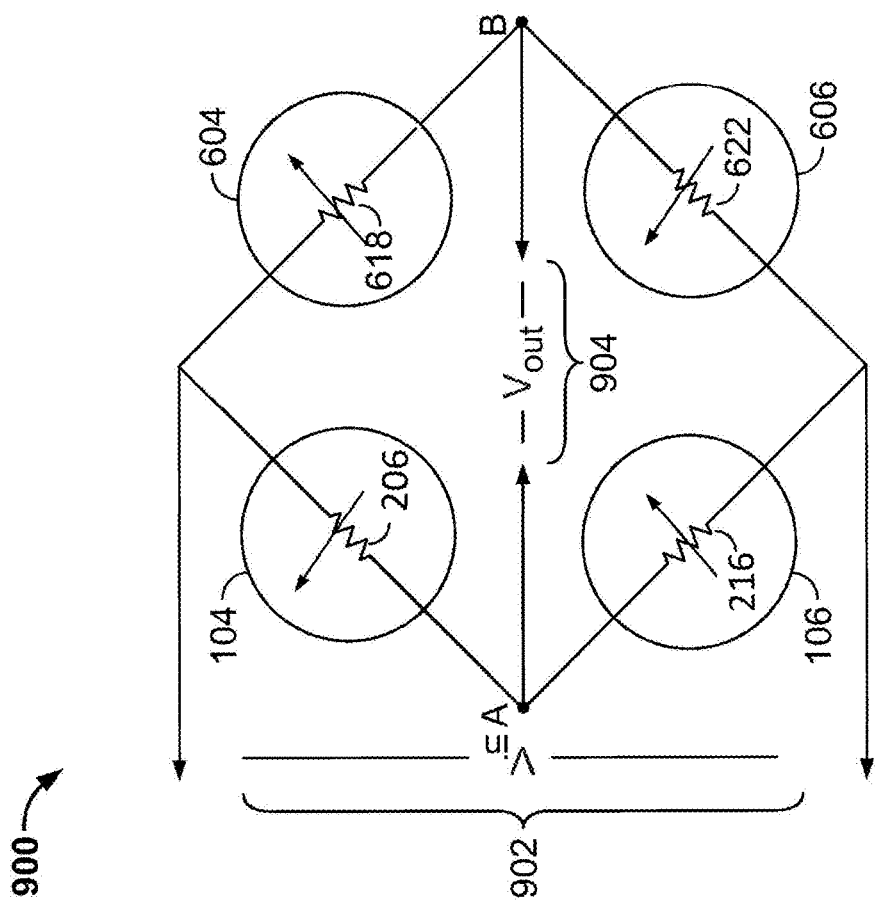
FIG. 9 shows an example circuit diagram depicting a Wheatstone bridge based on a plurality of gas sensors in accordance with an embodiment of the present disclosure.

FIG. 9 shows an example circuit diagram depicting a Wheatstone bridge based on a plurality of gas sensors in accordance with an embodiment of the present disclosure. In the exemplary embodiment of FIG. 9, the gas sensors 104, 106, 604, and 606 correspond to the gas sensors depicted and described in FIG. 6, although it will be understood that other gas sensor types, temperatures, and configurations may be utilized in other embodiments. Each of first sensing resistor 206, second sensing resistor 216, third sensing resistor 618, and fourth sensing resistor 622 are heated to a respective temperature or allowed to remain at the ambient temperature, as described herein. In an embodiment as described with respect to FIG. 6, first sensing resistor 206 and third sensing resistor 618 are heated to a common temperature at which both sensing resistors have a significant change in resistance (e.g., decrease) in response to an increase in CO2 content (e.g., at a temperature such as 100° C. near the peak of the CO2 output response curve). Second sensing resistor 216 may be at a temperature (e.g., ambient temperature) at which it is substantially insensitive to changes in CO2 or H2O. Fourth sensing resistor 622 may be at a temperature (e.g., 80° C.) where the response to CO2 is similar to the response of the first and third sensing resistors. These temperatures may be further selected such that the difference in output response due to changes in H2O between respective sets of sensing resistors (e.g., the difference in response between first sensing resistor 206 and second sensing resistor 216, versus the difference in response between third sensing resistor 618 and fourth sensing resistor 622) are equivalent.

Each of node 222 and node 252 correspond to resistor dividers across voltage Vin, with the value at each respective node changing based on the changes in resistance to the sensing resistors. Based on the relationships described above, a voltage of node 222 will increase as the CO2 concentration increases, based on the strong response first sensing resistor 206 to CO2 content and the lack of response of second sensing resistor 216 to CO2. Because third sensing resistor 618 and fourth sensing resistor 622 have an equivalent response to CO2, changes in CO2 will not change the voltage of node 252. Effects of temperature and H2O will be substantially cancelled out and/or compensated at the output 904, as described herein.

The foregoing description includes exemplary embodiments in accordance with the present disclosure. These examples are provided for purposes of illustration only, and not for purposes of limitation. It will be understood that the present disclosure may be implemented in forms different from those explicitly described and depicted herein and that various modifications, optimizations, and variations may be implemented by a person of ordinary skill in the present art, consistent with the following claims.

What is claimed is:

1. A sensor device including a plurality of sensors, comprising:
    a first sensor comprising a first sensing resistor, a first heating element, and a first hotplate configured to expose the first sensing resistor to the ambient air, wherein the first heating element and the first hotplate are further configured to raise the temperature of the first sensing resistor to a first temperature greater than an ambient temperature, wherein a resistance of the first sensing resistor varies based on the concentration of one or more gases in the ambient air and based on the ambient temperature;
    a second sensor comprising a second sensing resistor and a second hotplate configured to expose the second sensing resistor to the ambient air, wherein the second sensing resistor is at the ambient temperature of a sample of ambient air, wherein a resistance of the second sensing resistor varies based on the ambient temperature, wherein the first sensing resistor and the second sensing resistor are connected in a first series electrical circuit, and wherein a first measurement node is located between the first sensing resistor and the second sensing resistor in the first series electrical circuit; and
    processing circuitry coupled to the measurement node, wherein the processing circuitry is configured to determine a concentration of a gas of interest of one of the one or more gases based on a voltage of the first measurement node while the first sensing resistor is at the first temperature and the second sensing resistor is at the ambient temperature.

2. The sensor device of claim 1, wherein the first temperature corresponds to a temperature at which an increase in the concentration of the gas of interest results in a decrease in the resistance of the first sensing resistor.

3. The sensor device of claim 2, wherein the gas of interest comprises carbon dioxide (CO2).

4. The sensor device of claim 3, wherein the ambient temperature is in a range from 10 degrees Celsius to 40 degrees Celsius and the first temperature is in a range from 40 degrees Celsius to 200 degrees Celsius.

5. The sensor device of claim 2, wherein the first temperature corresponds to a temperature at which an increase in the concentration of a gas of that is not of interest of the one or more gases results in an increase in the resistance of the first sensing resistor.

6. The sensor device of claim 5, wherein the gas of interest is CO2 and the gas that is not of interest is water vapor (H2O).

7. The sensor device of claim 1, further comprising:
    a third sensor comprising a third sensing resistor, a third hotplate, and a second heating element, wherein the second heating element is configured to raise the temperature of the third sensing resistor to a third temperature greater than the ambient temperature; and
    a fourth sensor comprising a fourth sensing resistor, a fourth hotplate, and a third heating element, wherein the third heating element is configured to raise the temperature of the fourth sensing resistor to a fourth temperature greater than the ambient temperature,
    wherein the third hotplate is configured to expose the third sensing resistor to ambient air and the fourth hotplate is configured to expose the fourth sensing resistor to the ambient air,
    wherein the third sensing resistor and the fourth sensing resistor are connected in a second series electrical circuit, and wherein a second measurement node is located between the third sensing resistor and the fourth sensing resistor in the second series electrical circuit and coupled to the processing circuitry, and
    wherein the processing circuitry is further configured to determine the concentration of the gas of interest based on the voltage of the first measurement node and the voltage of the second measurement node.

8. The sensor device of claim 7, wherein the first sensing resistor, the second sensing resistor, the third sensing resistor, and the fourth sensing resistor are configured in a Wheatstone bridge, and wherein the processing circuitry is configured to determine the concentration of the gas of interest based on a measured value of the Wheatstone bridge.

9. The sensor device of claim 8, wherein the measured value corresponds to a voltage difference between the first measurement node and the second measurement node.

10. The sensor device of claim 7, wherein the processing circuitry comprises a differential amplifier, wherein the first measurement node is coupled to a first input node of the differential amplifier, the second measurement node is coupled to a second input node of the differential amplifier, and the processing circuitry determines the concentration of the gas of interest based on an output of the differential amplifier.

11. The sensor device of claim 7, wherein the processing circuitry comprises a temperature sensor, and the processing circuitry determines the concentration of the gas of interest based on the voltage at the first measurement node, the voltage at the second measurement node, and an output of the temperature sensor.

12. The sensor device of claim 7, wherein the first temperature and the third temperature are within approximately 50 degrees Celsius.

13. The sensor device of claim 1, wherein the second sensor further comprises a second heating element,
    wherein during a first time period the first heating element heats the first sensor to the first temperature and the second heating dement does not apply heat to the second sensor such that the temperature of the second sensor corresponds to the ambient temperature,
    wherein the processing circuitry is configured to determine a first value corresponding to a first voltage of the first measurement node during the first time period,
    wherein during a second time period the first heating element heats the first sensor to a second temperature greater than the ambient temperature and the second heating element heats the second sensor such to a third temperature greater than the ambient temperature,
    wherein the processing circuitry is configured to determine a second value corresponding to a second voltage of the first measurement node during the second time period, and wherein the processing circuitry is configured to determine the concentration of the gas of interest based on the first value and the second value.

14. The sensor device of claim 1, further comprising a first fixed resistor, wherein the first fixed resistor is located in the first series electrical circuit, wherein a second measurement node is located between the first fixed resistor and one of the first sensing resistor or the second sensing resistor, wherein the processing circuitry is configured to determine the concentration of the gas of interest based on the voltage of the first measurement node and the second measurement node.

15. The sensor device of claim 14, wherein the first the first fixed resistor is located between the first sensing resistor and the second sensing resistor in the first series electrical circuit.

16. The sensor device of claim 14, further comprising a second fixed resistor located in the first series electrical circuit, wherein the first measurement node is located at a connection between the first sensing resistor and the first fixed resistor, the second measurement node is located at a connection between the second sensing resistor and the second fixed resistor, and a third measurement node is located between the first fixed resistor and the second fixed resistor.

17. The sensor device of claim 16, wherein the first fixed resistor is located between the first sensing resistor and the second sensing resistor in the first series electrical circuit, and the second fixed resistor is between the first fixed resistor and the second sensing resistor.

18. The sensor device of claim 1, wherein the second sensor further comprises a second heating element, wherein the second heating element and the second hotplate are configured to raise the temperature of the second sensing resistor to a second temperature that is within 10 degrees Celsius of the ambient temperature.

\* \* \* \* \*

UNITED STATES PATENT AND TRADEMARK OFFICE
CERTIFICATE OF CORRECTION

PATENT NO.           : 12,044,644 B2
APPLICATION NO.      : 17/559839
DATED                : July 23, 2024
INVENTOR(S)          : Ilya Gurin It is certified that error appears in the above-identified patent and that said Letters Patent is hereby corrected as shown below:

In the Claims

In Column 23, Claim 3, Line 51, delete "(CO2)." and insert -- ($CO_2$). --, therefor.

In Column 23, Claim 6, Line 62, delete "CO2" and insert -- $CO_2$ --, therefor.

In Column 23, Claim 6, Line 63, delete "(H2O)." and insert -- ($H_2O$). --, therefor.

In Column 25, Claim 15, Line 13, delete "the first the" and insert -- the --, therefor.

Signed and Sealed this
Twenty-seventh Day of August, 2024

Katherine Kelly Vidal
*Director of the United States Patent and Trademark Office*